United States Patent
Morikawa et al.

(10) Patent No.: US 9,475,876 B2
(45) Date of Patent: Oct. 25, 2016

(54) ANTI ONCOSTATIN M RECEPTOR BETA ANTIBODY USED FOR TREATING ATOPIC DERMATITIS

(71) Applicants: WAKAYAMA MEDICAL UNIVERSITY, Wakayama (JP); SBI Biotech Co., Ltd., Tokyo (JP)

(72) Inventors: Yoshihiro Morikawa, Wakayama (JP); Tadasuke Komori, Wakayama (JP); Eiji Esashi, Tokyo (JP); Ayumi Kotaki, Tokyo (JP)

(73) Assignees: Wakayama Medical University, Wakayama (JP); SBI Biotech Co., Ltd., Tokyo (JP)

( * ) Notice: Subject to any disclaimer, the term of this patent is extended or adjusted under 35 U.S.C. 154(b) by 0 days.

(21) Appl. No.: 14/400,421

(22) PCT Filed: May 10, 2013

(86) PCT No.: PCT/JP2013/063734
§ 371 (c)(1),
(2) Date: Nov. 11, 2014

(87) PCT Pub. No.: WO2013/168829
PCT Pub. Date: Nov. 14, 2013

(65) Prior Publication Data
US 2015/0132303 A1 May 14, 2015

Related U.S. Application Data

(60) Provisional application No. 61/645,912, filed on May 11, 2012.

(51) Int. Cl.
C07K 16/28 (2006.01)
A61K 39/395 (2006.01)
A61K 39/00 (2006.01)

(52) U.S. Cl.
CPC ..... *C07K 16/2866* (2013.01); *A61K 2039/505* (2013.01); *C07K 2317/14* (2013.01); *C07K 2317/54* (2013.01); *C07K 2317/55* (2013.01); *C07K 2317/76* (2013.01)

(58) Field of Classification Search
None
See application file for complete search history.

(56) References Cited

U.S. PATENT DOCUMENTS 5,925,740 A * 7/1999 Mosley ............ C07K 14/70503
530/387.1

FOREIGN PATENT DOCUMENTS

| JP | 2005-247836 | 9/2005 |
| WO | 95/33059 A | 12/1995 |
| WO | 99/48523 A | 9/1999 |
| WO | 2006/084092 | 8/2006 |

OTHER PUBLICATIONS

Radka et al.—Abrogation of the antiproliferative activity of Oncostatin M by a monoclonal antibody—Cytokine, 4, 221-226, 1992.*
Mouse OSM-R beta mAb fact sheet—R &D systems, web accessed Feb. 2, 2016.*
Bando T, et al (2006) Complete overlap of interleukin-31 receptor A and oncostatin M receptor β in the adult dorsal root ganglia with distinct developmental expression patterns. Neuroscience 142:1263-1271. (Abstract only).
Bilsborough J, et al (2006) IL-31 is associated with cutaneous lymphocyte antigen-positive skin homing T cells in patients with atopic dermatitis. J Allergy Clin Immunol 117:418-425. (Abstract only).
Cooper KD (1994) Atopic dermatitis: recent trends in pathogenesis and therapy. J Invest Dermatol 102:128-137. (Abstract only).
Dillon SR, et al (2004) Interleukin 31, a cytokine produced by activated T cells, induces dermatitis in mice. Nat. Immunol 5:752-760. (Abstract only).
Dreuw A, et al (2004) Characterization of the signaling capacities of the novel gp130-like cytokine receptor. J Biol Chem 279:36112-36120. (Abstract only).
Espat NJ, et al. (1995) "PEG-BP-30 monotherapy attenuates the cytokine-mediated inflammatory cascade in baboon *Escherichia coli* septic shock", J Surg Res. 59(1):153-58 (Abstract only).
Grimstad O, et al (2008) Anti-interleukin-31-antibodies ameliorate scratching behavior in NC/Nga mice: a model of atopic dermatitis. Exp Dermatol 18:35-43. (Abstract only).
Hara T, et al (1999) Identification of podocalyxin-like protein 1 as a novel cell surface marker for hemangioblasts in the murine aorta-gonad-mesonephros region. Immunity11:567-78. (Abstract only).
Inoue J, and Aramaki Y (2007) Suppression of skin lesions by transdermal application of CpG-oligodeoxynucleotides in NC/Nga mice, a model of human atopic dermatitis. J Immunol 178:584-591. (Abstract only).
International Preliminary Report on Patentability for PCT/JP2013/063734, Jan. 21, 2014.
International Search Report for PCT/JP2013/063734, Jun. 11, 2013.
Mosley, B., et al (1996) "Dual Oncostatin M (OSM) Receptors", J Biol Chem. 271(50):32635-43.
Ogorochi, T., et al.,(1992) Monoclonal antibodies specific for low-affinity interleukin-3 (IL-3) binding protein AIC2A: evidence that AIC2A is a component of a high-affinity IL-3 receptor. Blood. 79:895-903. (Abstract only).
Sonkoly E, et al (2006) IL-31: A new link between T cells and pruritus in atopic skin inflammation. J Allergy Clin Immunol 117:411-417. (Abstract only).

(Continued)

*Primary Examiner* — Elly-Gerald Stoica
(74) *Attorney, Agent, or Firm* — Fish & Richardson P.C.

(57) ABSTRACT

A monoclonal antibody against oncostatin M specific receptor beta subunit, a hybridoma capable of producing the same and a medicament for treating atopic dermatitis comprising the same.

5 Claims, 13 Drawing Sheets

(56) References Cited

OTHER PUBLICATIONS

Tanaka M, et al (1999) Reconstitution of the functional mouse oncostatin M (OSM) receptor: molecular cloning of the mouse OSM receptor beta subunit. Blood 93: 804-15.
Tanaka M, et al (2003) Targeted disruption of oncostatin M receptor results in altered hemtopoiesis. Blood 102:3154-3162. (Abstract only).
Tanaka, M., et al. (1999) Reconstitution of the functional mouse oncostatin M (OSM) receptor: molecular cloning of the mouse OSM receptor beta subunit. Blood. 93:804-815. (Abstract only).
Wang H, et al. (2008) "The cytokine storm and factors determining the sequence and severity of organ dysfunction in multiple organ dysfunction syndrome", Am J Emerg Med. Jul. 2008; 26(6):711-15 (Abstract only).

\* cited by examiner

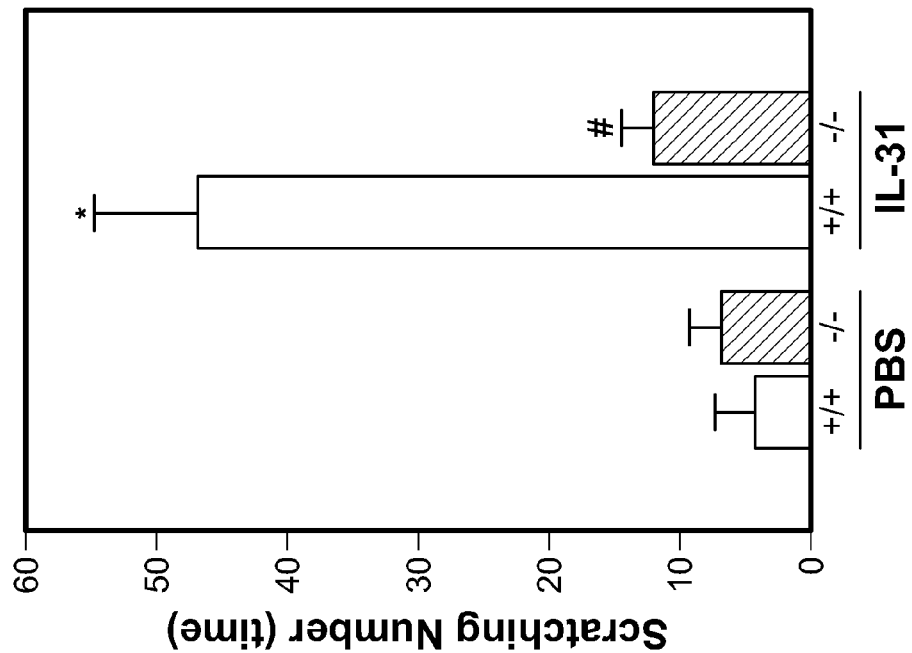
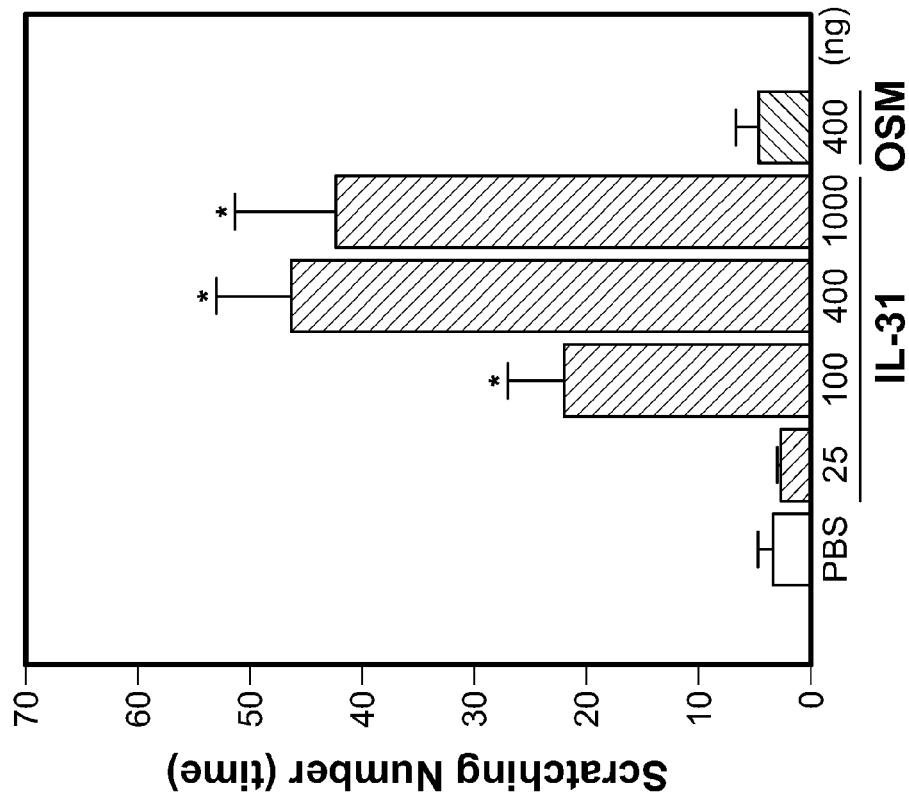

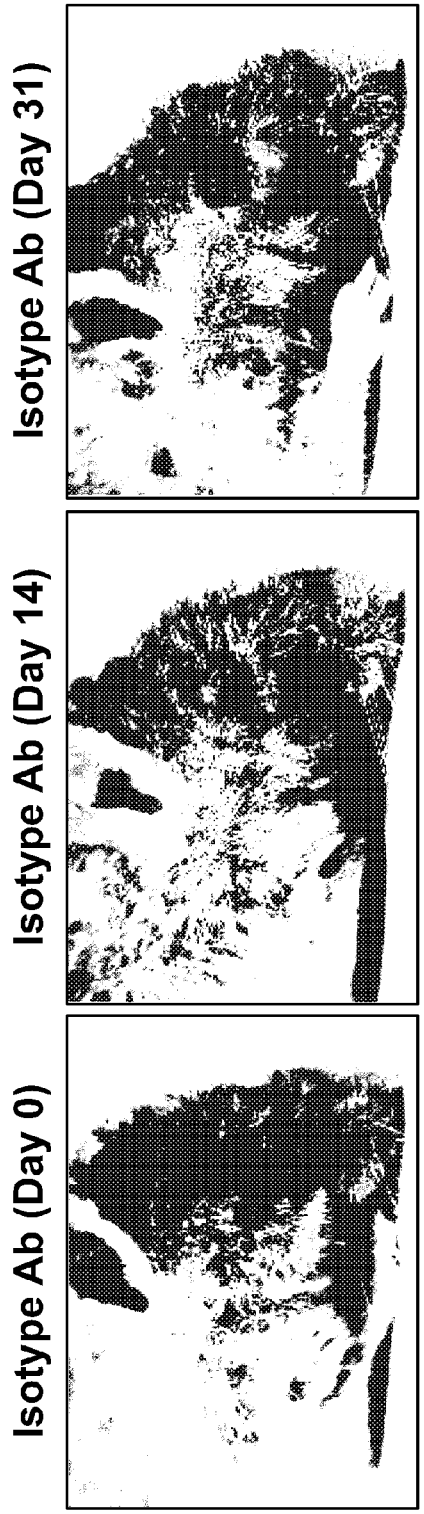

Isotype Ab (back)

OSMRβ Ab (back)

Isotype Ab (ear)

OSMRβ Ab (ear)

Isotype Ab (face)

OSMRβ Ab (face)

ANTI ONCOSTATIN M RECEPTOR BETA ANTIBODY USED FOR TREATING ATOPIC DERMATITIS

TECHNICAL FIELD

The present invention relates to an antibody against oncostatin M (OSM) receptor beta subunit (OSMRβ), a hybridoma capable of producing the monoclonal antibody and use of the monoclonal antibody for the treatment of OSM receptor-related diseases or disorders such like atopic dermatitis.

BACKGROUND ART

The immune system protects human body from bacterial, parasitic, fungal, viral infections and from the growth of tumor cells. However, the immune response can sometimes be unwanted and cause immune-mediated disorder. The disorder includes autoimmune disease, graft rejection, hypersensitivity, diseases associated with the over-stimulation of host's immune system by microbes. The autoimmune diseases result from immune responses against endogenous and/or exogenous antigens. Foreign substances, derived from bacteria, parasites, fungi or viruses, may mimic self-proteins and cause the immune system to erroneously launch an immune attack on self-cells and tissues, resulting in onset of the autoimmune diseases. The graft rejection is caused by the immune response in the transplant recipient (host) against the transplanted organ/tissue. When a subject is transplanted with grafts including kidney, pancreas, heart, lung, bone marrow, cornea and skin, the subject can launch an immune response (rejection) against the grafts. Hypersensitivity is an inappropriate immune response that has deleterious effects, resulting in significant tissue damage or even death. The response is characterized by the overproduction of cytokines. The exaggerated production of cytokines is known to contribute to sepsis characterized by cytokine-mediated lethal shock (Espat N J, et al. J Surg Res. 1995 July; 59 (1):153-8). Multiple organ dysfunction syndromes (MODS) are a major cause of morbidity and mortality in severe sepsis and shock. Cytokine-mediated lethal shock resulted from over-production of host cytokines is considered a main mechanism leading to MODS (Wang H, et al. Am J Emerg Med. 2008 July; 26 (6):711-5).

Atopic dermatitis is a pruritic inflammatory skin disease. The conventional medicinal agent for treating the atopic dermatitis is mainly a topical cream comprising as an active ingredient steroid compounds. However, such available medical agents are not always effective in the most critical symptoms such like pruritus in addition of exhibiting serious side effects caused by steroid compounds per se. Thus, the alternative agent possessing potent effect against pruritus and no serious side effect is expected to be provided.

The demonstrated in vivo activities of the cytokine family illustrate the enormous clinical potential of, and need for, other cytokines, cytokine agonists, and cytokine antagonists. Recently, several investigators have reported that interleukin (IL)-31 is involved in the pathogenesis of atopic dermatitis. Functional IL-31 receptor consists of IL-31 specific receptor A (IL-31Ra) and OSMRβ.

Oncostatin M (OSM) is a member of the IL-6 family of cytokines and its receptor consists of the OSM specific receptor beta subunit (OSMRβ) and gp130, the common receptor subunit of this cytokine family. OSM is produced by a variety of cells such as hematopoietic cells and fibroblasts and is suggested to play a role in immune reactions and hematopoiesis, while both OSM-deficient mice and OSMRβ-deficient mice developed normally and were fertile (Tanaka et al., 2003).

Interleukin-31 is produced by activated $CD4^+T$ cells. Overexpression of IL-31 in transgenic mice results in a pruritic skin condition that is similar to human atopic dermatitis (Dillon et al., 2004). Analysis of IL-31 levels in human dermatitis samples has shown increased expression of IL-31 in atopic dermatitis compared with healthy control populations, implicating involvement of IL-31 in the pathogenesis of allergic skin diseases (Bilsborough et al., 2006; Sonkoly et al., 2006). IL-31 receptor alpha (IL-31Ra) pairs with OSMRβ to form the functional heterodimer receptor for IL-31 (Dillon et al., 2004). In addition, the present inventors have demonstrated complete co-localization of IL-31Ra and OSMRβ in both a subset of small-sized dorsal root ganglion (DRG) neurons and afferent fibers in the spinal cord and the dermis of the skin (Bando et al, 2006). Thus, IL-31 might be related to the pathogenesis of the dermatitis. However, treatment of NC/Nga mice with severe atopic dermatitis with anti-IL-31 antibody failed to ameliorate skin lesions in spite of the reduction of scratching behavior (Grimstad et al., 2008), suggesting that blocking of IL-31 is not enough to prevent atopic dermatitis development.

Nucleic acid and amino acid sequences of OSMRβ are known and sequenced (SEQ. ID Nos. 1 and 2, respectively), and OSMRβ is suggested to be associated with the biological activities mediated by OSM (WO95/33059).

It is known that an antagonist of OSM such as an antibody thereto or a small molecule can be used for the treatment or prophylaxis of an inflammatory arthropathy or inflammatory disorder, and for screening for such antagonists (WO99/48523).

One of the present inventors studied actions of OSM on a pain-responsive neuron and provided a pharmaceutical composition for treating pains, especially treatment-resistant pain such as cancerous pain, neurogenic pain and inflammatory pains, which contains an OSM antagonist or the OSM or contains a transgenic vector containing a nucleic acid in which a cytotoxic gene is linked to a promoter of an OSM receptor beta-chain gene (JP 2005-247836 A).

In the previous report, the present inventors have demonstrated that OSMRβ and IL-31Ra were co-expressed in the same subset of small-sized nociceptive neurons of adult dorsal root ganglia (DRGs).

DISCLOSURE OF INVENTION

The present inventions relate to an antibody against oncostatin M (OSM) receptor beta subunit (OSMRβ), a hybridoma capable of producing the monoclonal antibody and use of the monoclonal antibody for the treatment of OSM receptor-related diseases or disorders such like atopic dermatitis.

Problem to be Solved by the Invention

The present invention addresses these needs by providing the antibody to pro-inflammatory cytokine receptor, namely OSM receptor (OSMR). Such antibody of the present invention, which may block, inhibit, reduce antagonize or neutralize the activity of OSM. The invention further provides uses therefor in inflammatory disease, as well as related compositions and methods.

Means for Solving the Problem

To examine a role of OSM and IL-31 during atopic dermatitis development, the present inventors eagerly studied OSMRβ and antibodies against the same and developed anti-OSMRβ specific monoclonal antibody 7D2, and then evaluated the function of the antibody in atopic dermatitis mice.

The present inventors investigated the function of the signaling from OSMRβ with itch and/or skin lesions of atopic dermatitis. In OSMRβ-deficient mice, IL-31-induced itch responses were abolished, indicating that IL-31 evokes itch through OSMRβ. Then, the present inventors developed anti-OSMRβ specific antibody for further animal studies. The present inventors evaluated the function of the antibody in NC/Nga mice, which developed skin lesions that were similar to human atopic dermatitis. The subcutaneous application of anti-OSMRβ antibody decreased scratching behavior with dramatic amelioration of the skin lesions in the NC/Nga mice. In addition, the elevation of total serum IgE was suppressed and serum IL-13 level was decreased in the anti-OSMRβ antibody-treated mice.

These findings indicate that the OSMRβ is provided as a potential molecular target for therapeutic intervention and anti-OSMRβ specific antibody is effective for immunotherapy in patients with atopic dermatitis. Based on these findings, the present inventors have completed the invention.

Thus, the present inventions are as follows:
(1) A hybridoma cell line deposited as Accession No. FERM ABP-11380.
(2) A monoclonal antibody against oncostatin M specific receptor beta subunit, obtained from the hybridoma according to (1).
(3) An active fragment of the antibody according to (2), selected from the group consisting of a Fab, Fab', F(ab')$_2$, and scFv.
(4) An inhibitor against the signal pathways between OSM and OSM receptor and between IL-31 and IL-31 receptor, comprising the monoclonal antibody according to (2) or the fragment according to (3).
(5) A medicament for treating atopic dermatitis comprising the monoclonal antibody according to (2) or the fragment according to (3).
(6) Use of the monoclonal antibody according to (2) or the fragment according to (3) for manufacturing the medicament for treating atopic dermatitis.
(7) A method for treating atopic dermatitis comprising a therapeutically effective amount of the monoclonal antibody according to (2) or the fragment according to (3) with a pharmaceutically acceptable carrier, excipient or diluent.
(8)' A method for isolation and identification of a molecule possessing more potent binding activity against OSMRβ as well as against OSM receptor consisting of OSMRβ and gp130 in comparison with the monoclonal antibody according to (2), comprising the following steps:
 1) preparing and incubating said molecule with (a) the cells expressing OSMRβ and expressing no gp130, and with (b) the cells expressing OSM receptor, in the presence of the monoclonal antibody according to (2); and
 2) indirectly investigating whether said molecule can competitively bind to both of said cells by measuring the binding of the monoclonal antibody according to (2) to both of said cells.
(9) A method for isolation and identification of a molecule possessing more potent inhibition activities against OSM and/or IL-31 signal pathways in comparison with the monoclonal antibody according to (2), comprising the following steps:
 1) preparing and incubating said molecule with the cells expressing OSM receptor and IL-31 receptor; and
 2) investigating whether said molecule can more significantly suppress the phosphorylation activity induced by signal transduction from OSM to OSM receptor and/or from IL-31 to IL-31 receptor in comparison with the monoclonal antibody according to (2).

BRIEF DESCRIPTION OF THE DRAWINGS

FIGS. 1A and 1B show induction of scratching behavior by IL-31 in mice. FIG. 1A shows scratching behavior induced by IL-31 in C57BL/6J mice (n=4 per groups). Mice were injected PBS (white bar), IL-31 (25-1000 ng; black bars), or OSM (400 ng; gray bar) in the rostral part of the back skin intradermally. FIG. 1B shows scratching behavior induced by IL-31 in OSMRβ$^{+/+}$ and OSMRβ$^{-/-}$ mice (n=4 per groups). OSMRβ$^{+/+}$ (white bars) and OSMRβ$^{-/-}$ (black bars) mice were injected PBS or IL-31 (400 ng) in the rostral part of the back skin intradermally. Scratching behavior was counted for 2 hours. Data represent the means+SEM. *$P<0.05$ versus PBS-injected mice in A. *$P<0.05$ versus PBS-injected OSMRβ$^{+/+}$ mice in B. #$P<0.05$ versus IL-31-injected OSMRβ$^{+/+}$ mice in B, Student's t-test. FIG. 2A shows that Ba/F3-mOSMRβ transfectants were stained with 7D2 hybridoma supernatant. Isotype control staining; gray shaded, 7D2 staining; bold line. FIG. 2B shows isotyping test of 7D2 monoclonal antibody. Isotype of 7D2 monoclonal antibody was determined as rat IgG1 kappa. FIG. 2C shows purification of 7D2 monoclonal antibody. Purity of 7D2 monoclonal antibody was evaluated with SDS-PAGE followed by CBB staining. 1 µg of purified 7D2 monoclonal antibody was loaded. FIG. 2D shows that Ba/F3-mOSMRβ and Ba/F3-mIL31Ra transfectants were stained with anti-OSMRβ (7D2) or anti-IL31Ra antibody (antibody concentration: 5 µg/ml). Note that 7D2 monoclonal antibody was specifically stained for BaF3-mOSMRβ but not for BaF3-mIL31Ra.

FIG. 3A shows that LO cells express OSMRβ and gp130. The cells were stained with anti-OSMR antibodies. Antibody 30-1 was purchased from MBL. Both 7D2 and 30-1 monoclonal antibodies stained LO cells while 7D2 monoclonal antibody had better staining ability for Ba/F3-mOSMRβ than for 30-1 (antibody concentration: 5 µg/ml). FIG. 3B shows affinity evaluation of anti-OSMR antibodies. Ba/F3-mOSMRβ or LO cells were stained with several concentration of the antibodies 7D2 and 30-1. After flow cytometric analysis, the percentage of stained cells (% of positive cells) was plotted with the antibody concentrations. X axis: antibody concentration (µg/ml), Y axis: percentage of the stained cells at the antibody concentration.

FIG. 3C shows that stimulation of OSM or IL-31 can induce the phosphorylation of Erks. FIG. 3D indicates that 7D2 monoclonal antibody can suppress the Erk phosphorylation caused by stimulation of OSM or IL-31, suggesting that 7D2 monoclonal antibody can inhibit the signal pathways of OSM/OSM receptor and IL-31/IL-31 receptor.

Figure 2A:
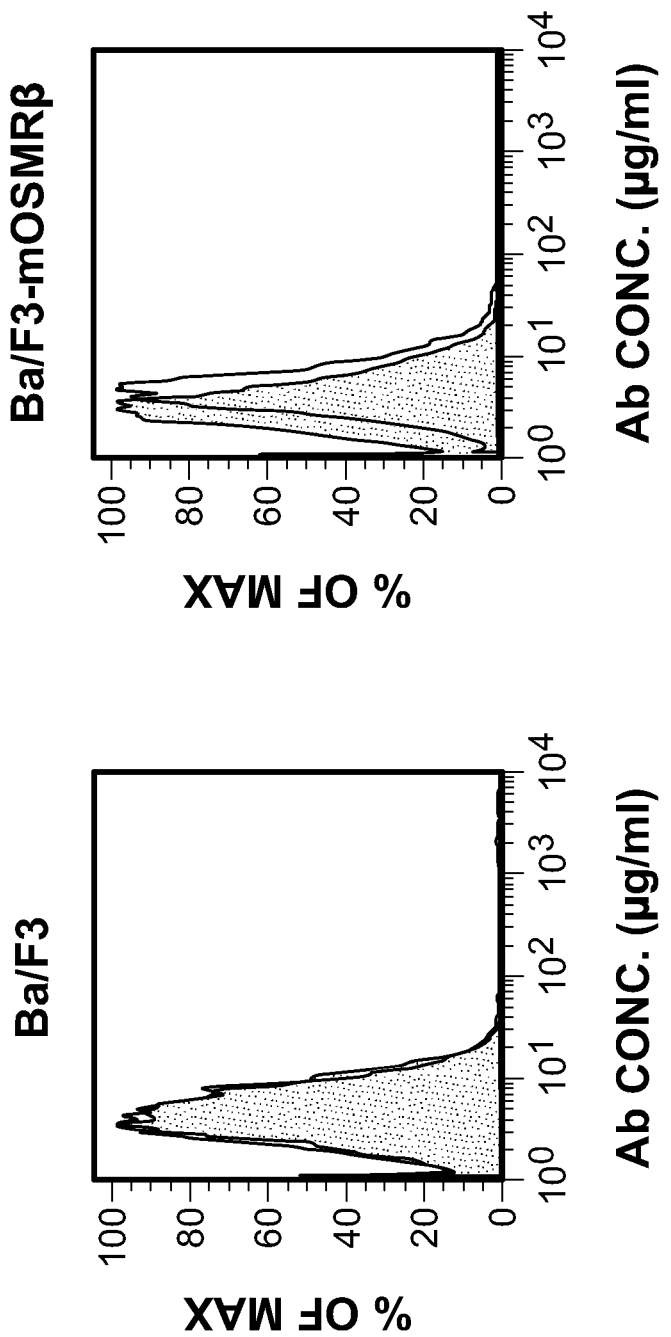
FIGS. 2A-2D show generation of anti-OSMRβ antibody (7D2).

7D2 monoclonal antibody (dotted line: n=7) or its isotype control antibody (solid line: n=6) at two times (day 0 and day 14). Scratching behavior was counted for 2 hours on days 0, 14, 24, and 31. Data represent the means+SEM. ANOVA followed by the post hoc Bonferroni test.

FIGS. 5A-F show effects of an anti-OSMRβ antibody on macroscopic observations of skin lesions in NC/Nga mice. NC/Nga mice were implanted with a hydrogel incorporated with anti-OSMRβ 7D2 monoclonal antibody (FIGS. 5D-F) or its isotype control antibody (FIGS. 5A-C) at two times (day 0 and day 14). Representative photographs on day 0 (FIGS. 5A and D), day 14 (FIGS. 5B and E), and day 31 (FIGS. 5C and F) were shown.

Figure 6A:
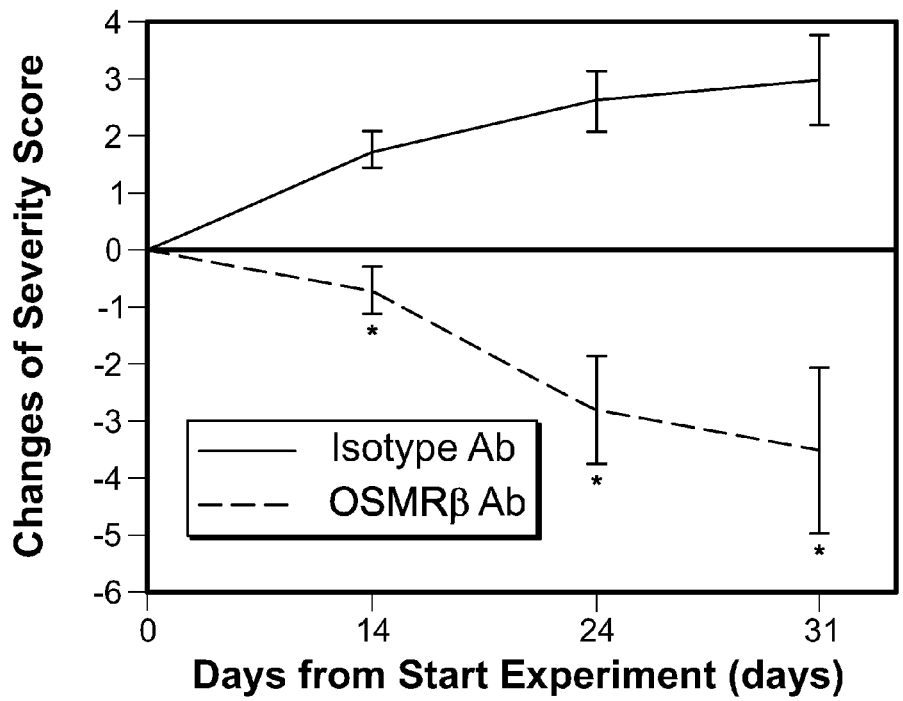
Figure 6B:
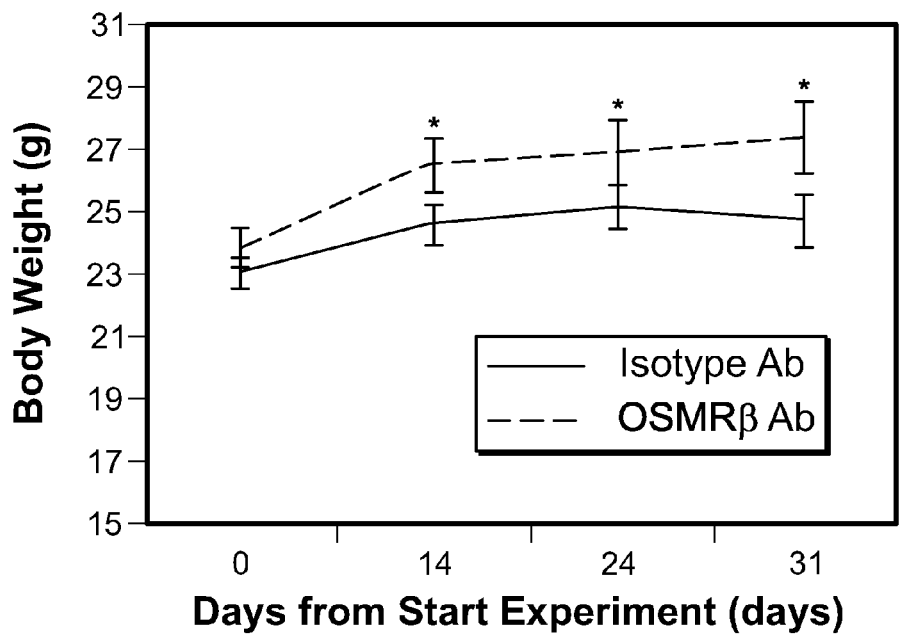
Figure 7A:
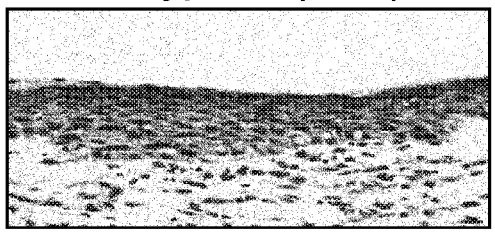
Figure 7B:
Figure 7C:
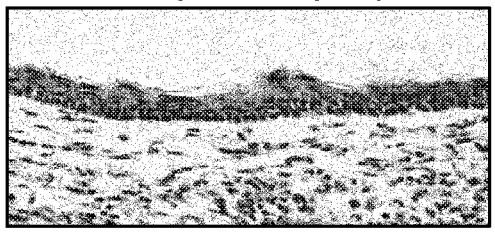
Figure 7D:
Figure 7E:
Figure 7F:
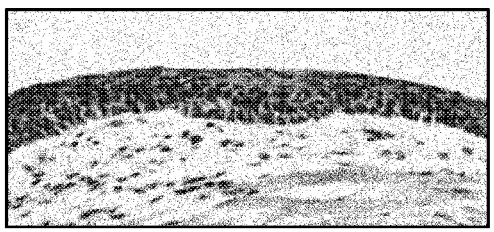

FIGS. 6A-6B show effects of an anti-OSMRβ antibody on dermatitis of NC/Nga mice. NC/Nga mice were implanted with a hydrogel incorporated with anti-OSMRβ 7D2 monoclonal antibody (dotted lines; n=8) or its isotype control (solid lines: n=10) at two times (day 0 and day 14). Skin severity score (FIG. 6A) and body weights (FIG. 6B) were measured on day 0, 14, 24, and 31. Skin severity score was shown as changes of the scores from day 0 of the experimental period. Data represent the means+SEM. *$P<0.05$, ANOVA followed by the post hoc Bonferroni test.

FIGS. 7A-F show effects of an anti-OSMRβ antibody on histopathological feature of skin lesions in NC/Nga mice. NC/Nga mice were implanted with a hydrogel incorporated with anti-OSMRβ 7D2 monoclonal antibody (FIGS. 7B, D, and F) or its isotype control antibody (FIGS. 7A, C, and E) at two times (day 0 and day 14). Representative photomicrographs of hematoxylin and eosin-stained sections in the back (FIGS. 7A and B), ear (FIGS. 7C and D), and face (FIGS. 7E and F) were shown. Scale bars=200 μm.

Figure 8A:
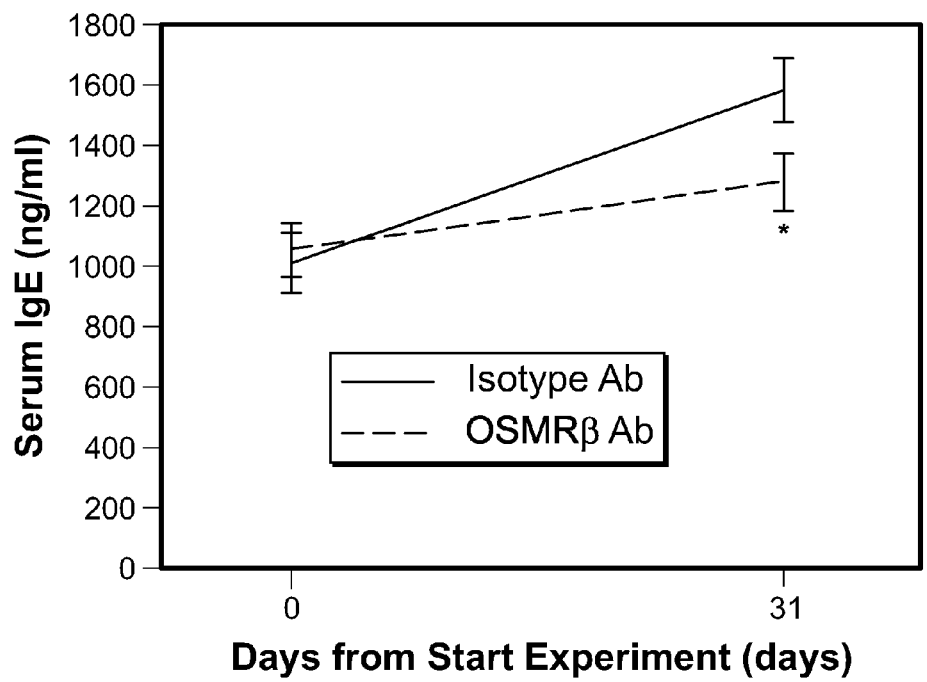
Figure 8B:
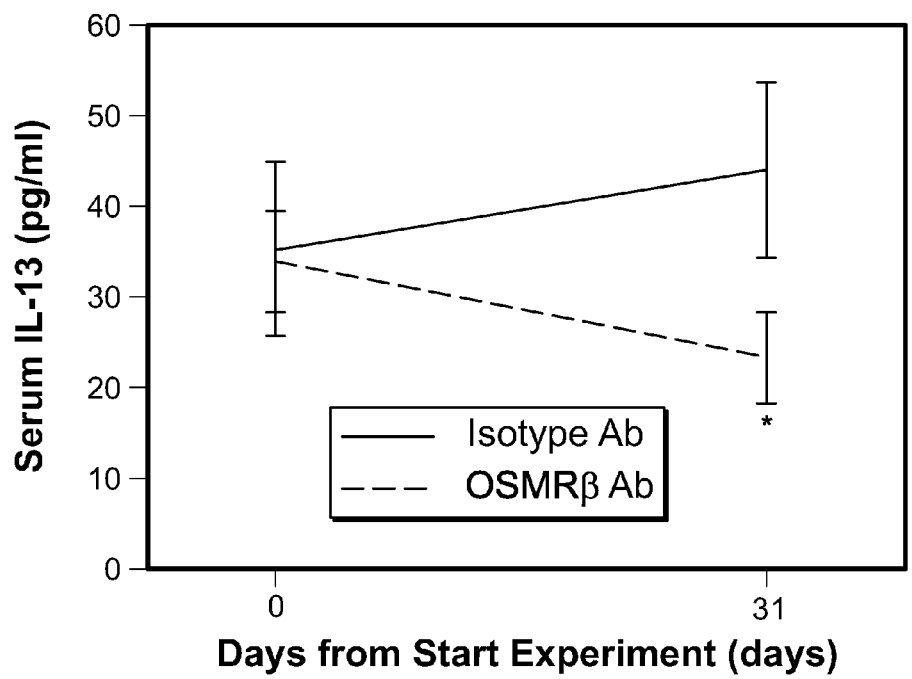

FIGS. 8A-B show effects of anti-OSMRβ antibody on serum IgE and IL-13 concentration of NC/Nga mice. NC/Nga mice were implanted with a hydrogel incorporated with anti-OSMRβ 7D2 monoclonal antibody (dotted line: n=4) or its isotype control antibody (solid line: n=4) at two times (day 0 and day 14). The concentration of serum IgE (FIG. 8(A)) and IL-13 (FIG. 8(B)) were measured on day 0 and 31. *$P<0.05$, ANOVA followed by the post hoc Bonferroni test.

Figure 9:
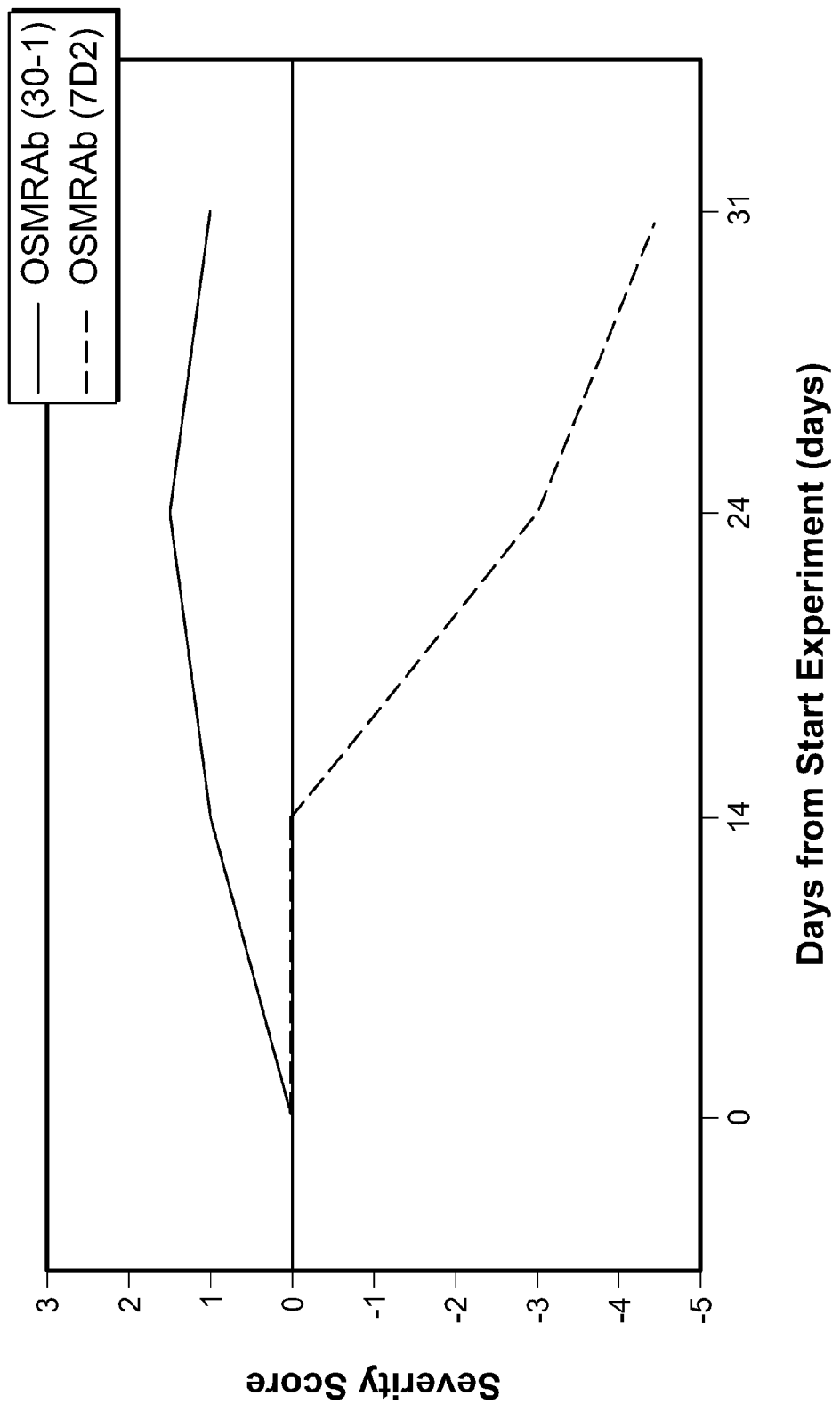

FIG. 9 shows effects of anti-OSMR antibodies on dermatitis of NC/Nga mice. NC/Nga mice were implanted with a hydrogel incorporated with an anti-OSMRβ antibody; 7D2 (dotted lines) or another anti-OSMR antibody; 30-1 (solid line) at two times (day 0 and day 14). Skin severity score was shown as changes of the scores from day 0 of the experimental period. All experimental procedures are same as described in FIG. 6.

EXAMPLE

The present inventions can be exemplified in the following Examples but should be not limited thereto.
Materials and Methods
1. Antibodies Antibodies listed below were used in the experiments. PE conjugated anti-Rat Ig k light chain (BD Pharmingen), anti-mouse OSMR (30-1, MBL), goat anti-mIL-31Ra antibody (R&D Systems), purified rat IgG2a k isotype control (R35-95, BD Pharmingen) and rat IgG1 isotype control (Clone 43414, R&D Systems). Isotype control antibody exhibited a low background binding on a variety of mouse tissues. Anti-phospho-p44/42 MAP kinase (Thr202/Tyr204) antibody was purchased from Cell Signaling (Cat#9101).

2. Mice

In the present study, 8-week-old C57BL/6J male mice (Clea Japan, Tokyo, Japan) were used. OSMRβ-deficient (OSMRβ$^{-/-}$) mice were made as described previously (Tanaka et al., 2003). Eight-week-old OSMRβ$^{+/+}$ and OSMRβ$^{-/-}$ male mice were used. NC/Nga mice with moderate to severe atopic dermatitis were purchased from SLC (Hamamatsu, Shizuoka, Japan) and kept in conventional conditions until the end-point of the experiments. Twelve-week-old NC/Nga male mice were used in the present study. All mice were kept under a 12-hour light/dark cycle with food and water ad libitum. At all times, the experiments were carried out under the control of the Animal Research Control Committee in accordance with The Guidelines for Animal experiments of Wakayama Medical University, Japanese Government Notification on Feeding and Safekeeping of Animals (No. 6), and the National Institute of Health Guide for the Care and Use of Laboratory Animals (NIH publication No. 80-23) revised 1978. All efforts were made to minimize the number of animals used and their suffering.

3. Generation of Ba/F3 Transfectants Expressing Murine IL-31Ra (mIL-31Ra)

mIL-31Ra gene (SEQ. ID No. 3) was cloned from murine dorsal root ganglia and subcloned into a retrovirus vector, pMXs-puro. Retrovirus carrying mIL-31Ra was produced and Ba/F3 cells were infected with the virus. The infected cells were selected with puromycin. Surface expression of mIL-31Ra (SEQ. ID No. 4) was confirmed by goat anti-mIL-31Ra antibody staining (R&D Systems) with FACS Calibur (BD).

Example 1

Generation of Anti-Murine Oncostatin M Receptor β (mOSMRβ) Monoclonal Antibody

The expression vector carrying soluble form of OSMRβ (SEQ. ID No. 5) was cloned into the expression vector which contains the sequences encoding the CD8 signal sequence linked with the FLAG tag and poly-histidine residues. The recombinant soluble OSMRβ (SEQ. ID No. 6) was produced in COST cells and purified with Ni-NTA and anti-FLAG M2 affinity column. Wistar rats were immunized with purified soluble mOSMRβ. Lymphocytes were recovered from the lymph nodes and fused with mouse myeloma P3X cells as described in Ogorochi, T et al, 1992. These cells were cultured in HAT medium to select hybridomas (fused cells). Hybridoma supernatants were screened for the production of anti-mOSMRβ antibody with Ba/F3 transfectant expressing mOSMRβ (Tanaka et al., 1999). Hybridoma cells producing anti-mOSMRβ antibodies were further cloned by single cell sorting with FACS Aria (Becton). Total 166 hybridoma clones were screened and hybridoma clone called 7D2 was selected as anti-mOSMRβ antibody producer for further analysis (FIG. 2A).

This hybridoma 7D2 has been deposited as Accession No. FERM ABP-11380 on Apr. 22, 2011 with International Patent Organism Depositary (IPOD), National Institute of Advanced Industrial Science and Technology (AIST), Tsukuba Central 6, 1-1-1 Higashi, Tsukuba, Ibaraki 305-8566 Japan.

Example 2

Figure 2B:
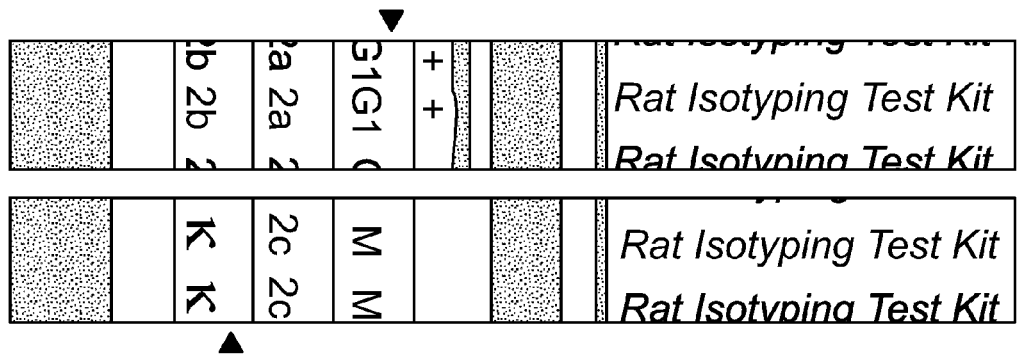
Figure 2C:
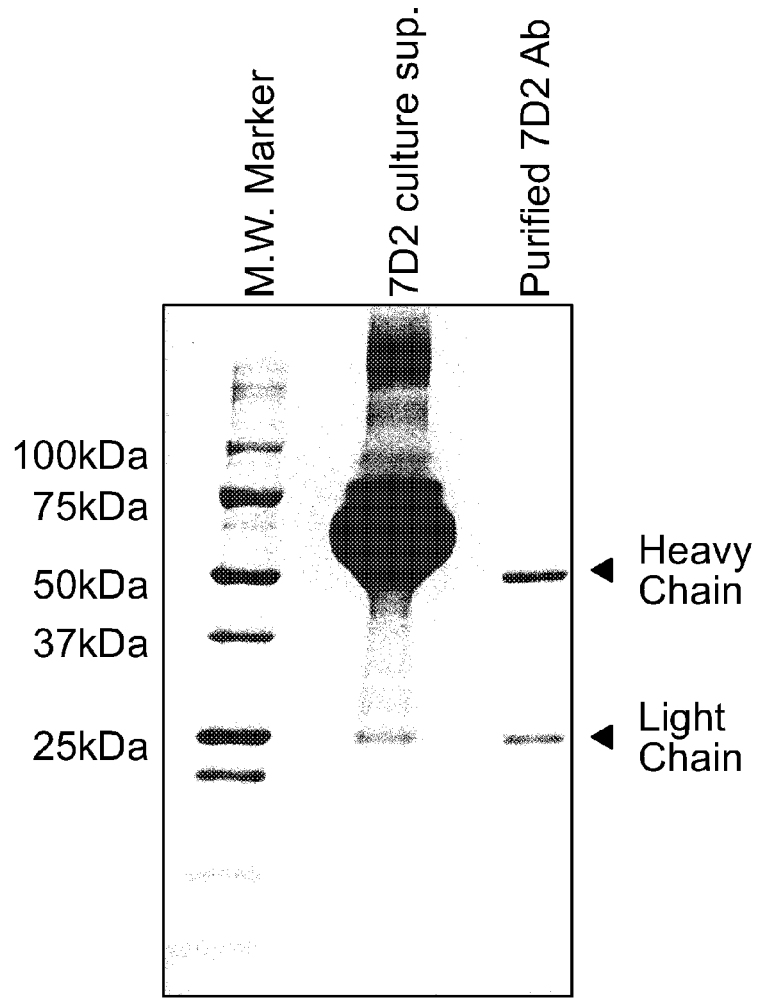
Figure 2D:
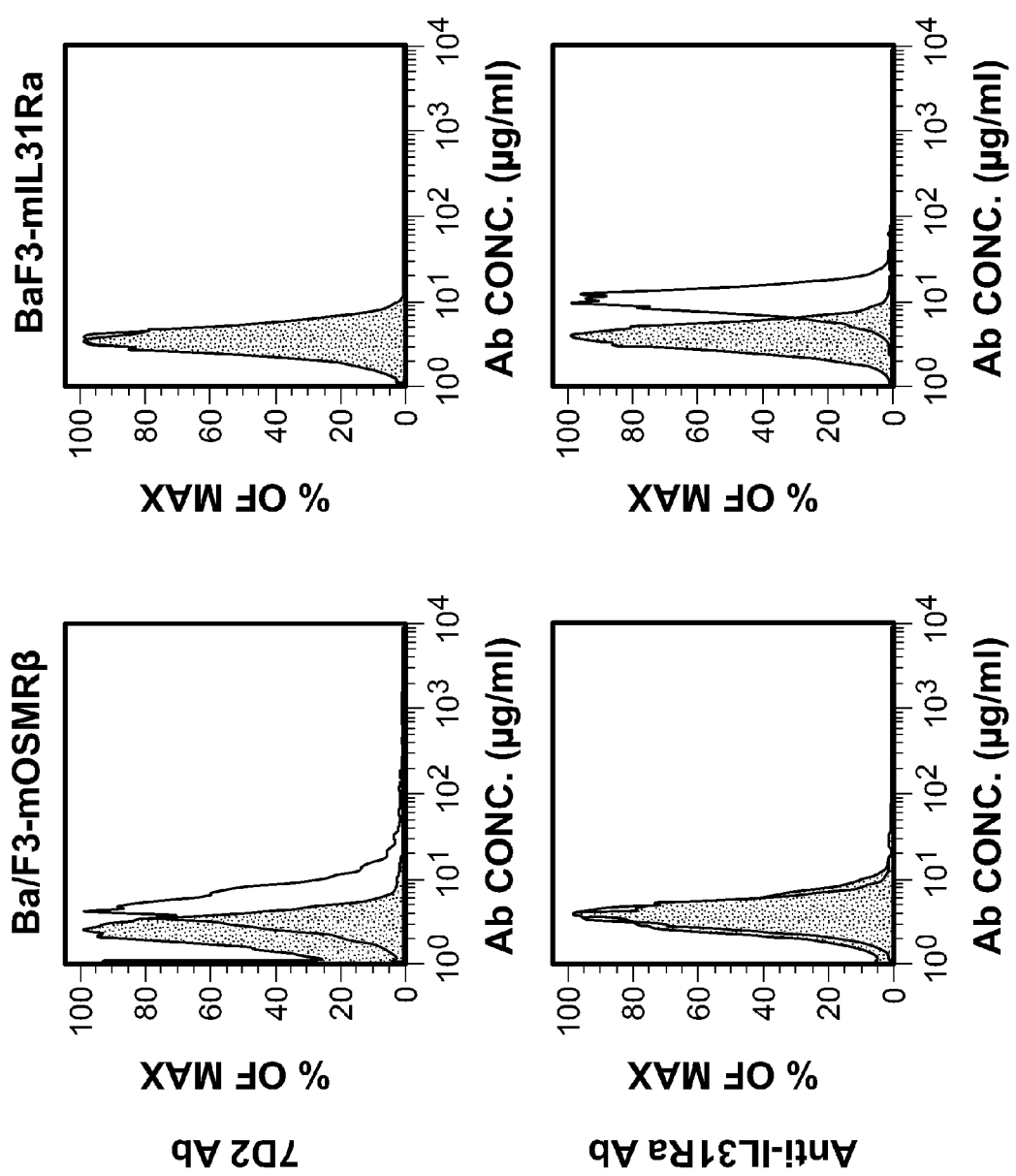

Purification and Preparation of Anti-mOSMRβ Antibody (7D2 Monoclonal Antibody) or Active Fragments Thereof Hybridoma culture supernatant was recovered and isotype of 7D2 monoclonal antibody was evaluated with Rat Monoclonal Antibody Isotyping Test Kit (Serotec). Isotype of 7D2 monoclonal antibody was confirmed as rat IgG1 (FIG. 2B). To purify the antibody, AKTA system (GE healthcare) with protein L column (Pierce) was applied. The culture supernatant from 7D2 hybridoma was passed through the protein L column and the bound antibody was eluted from the column as described in manufacture's protocol. The buffer of 7D2 monoclonal antibody solution was exchanged to Phosphate Buffered Saline (PBS). Purity of the 7D2 monoclonal antibody was evaluated by SDS-PAGE followed with CBB staining (FIG. 2C). The purified 7D2 monoclonal antibody was evaluated with BaF3 transfectant expressing mOSMRβ (BaF3-mOSMRβ). The purified 7D2 monoclonal antibody could stain BaF3-mOSMRβ. Specific binding of 7D2 monoclonal antibody to mOSMRβ was further confirmed by staining of BaF3-mOSMRβ cells and BaF3-mIL31Ra cells. 7D2 monoclonal antibody stained only BaF3-mOSMRβ cells but not BaF3-mIL-31Ra cells (FIG. 2D).

In further embodiments, the isolated monoclonal antibody is further subjected to conventional methods such like treatment of protease (i.e., papain, pepsin and the like) and linker conjugation in order to obtain active fragment thereof such like a Fab, Fab', F(ab')$_2$, and scFv.

Example 3

Characterization of Anti-mOSMRβ Antibody (7D2 Monoclonal Antibody)

Ba/F3 transfectants expressing mOSMRβ were incubated with purified 7D2 monoclonal antibody or commercially available anti-mOSMR Antibody (clone:30-1, MBL) at several concentrations. After washing the cells with PBS, the cells were incubated with PE conjugated anti-rat IgGs. After washing with PBS, the cells were analyzed with FACS Calibur (Becton). LO cells (Hara et al., 1999) which endogenously express both mOSMRβ and gp130 were stained with the 7D2 or the 30-1 monoclonal antibody as described above and analyzed with FACS Calibur. To evaluate specificity of 7D2 monoclonal antibody to mOSMRβ, 7D2 monoclonal antibody was examined with BaF3 transfectant expressing mIL-31Ra.

Figure 3A:
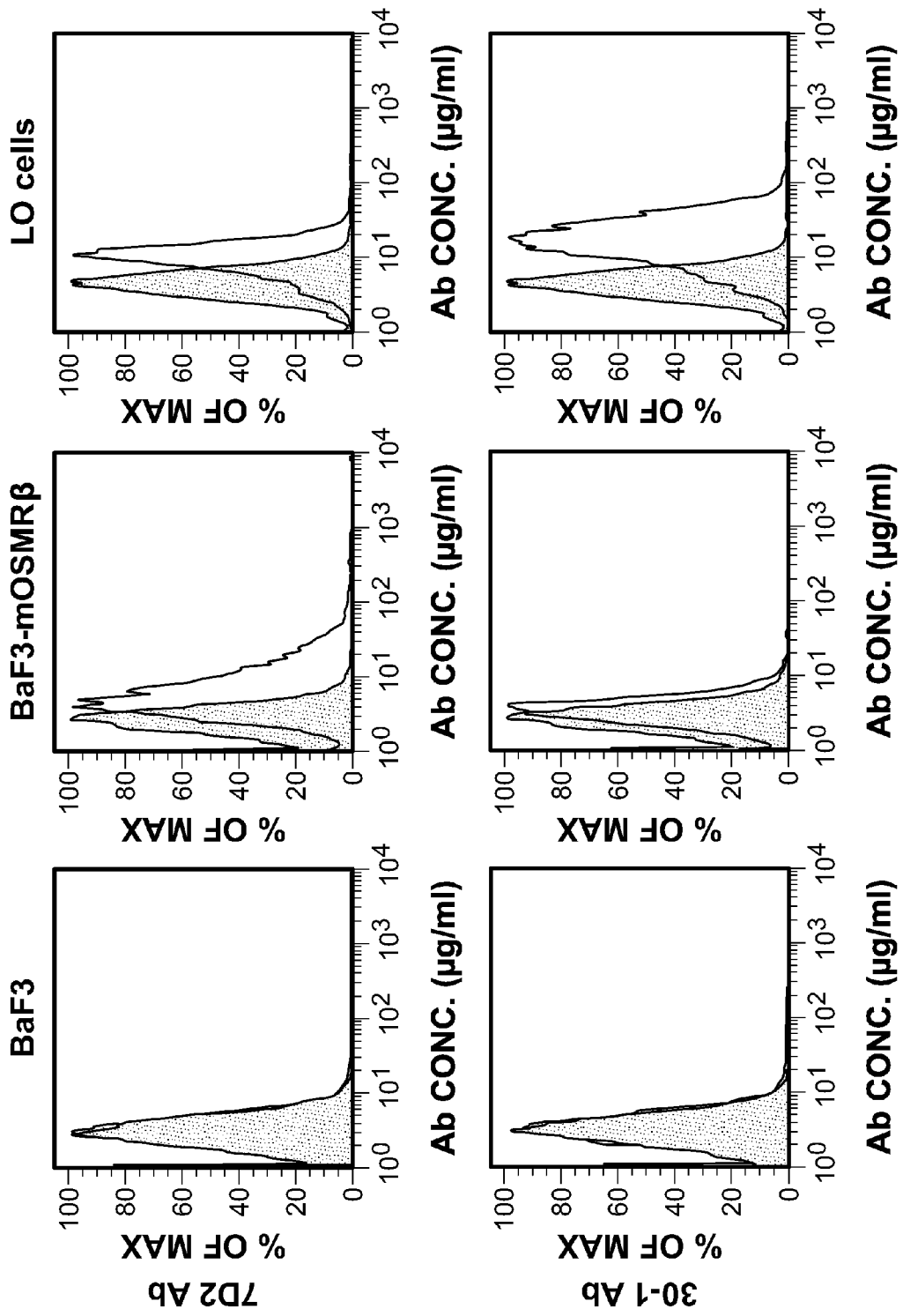
FIGS. 3A and 3B show characterization of 7D2 monoclonal antibody.
Figure 3B:
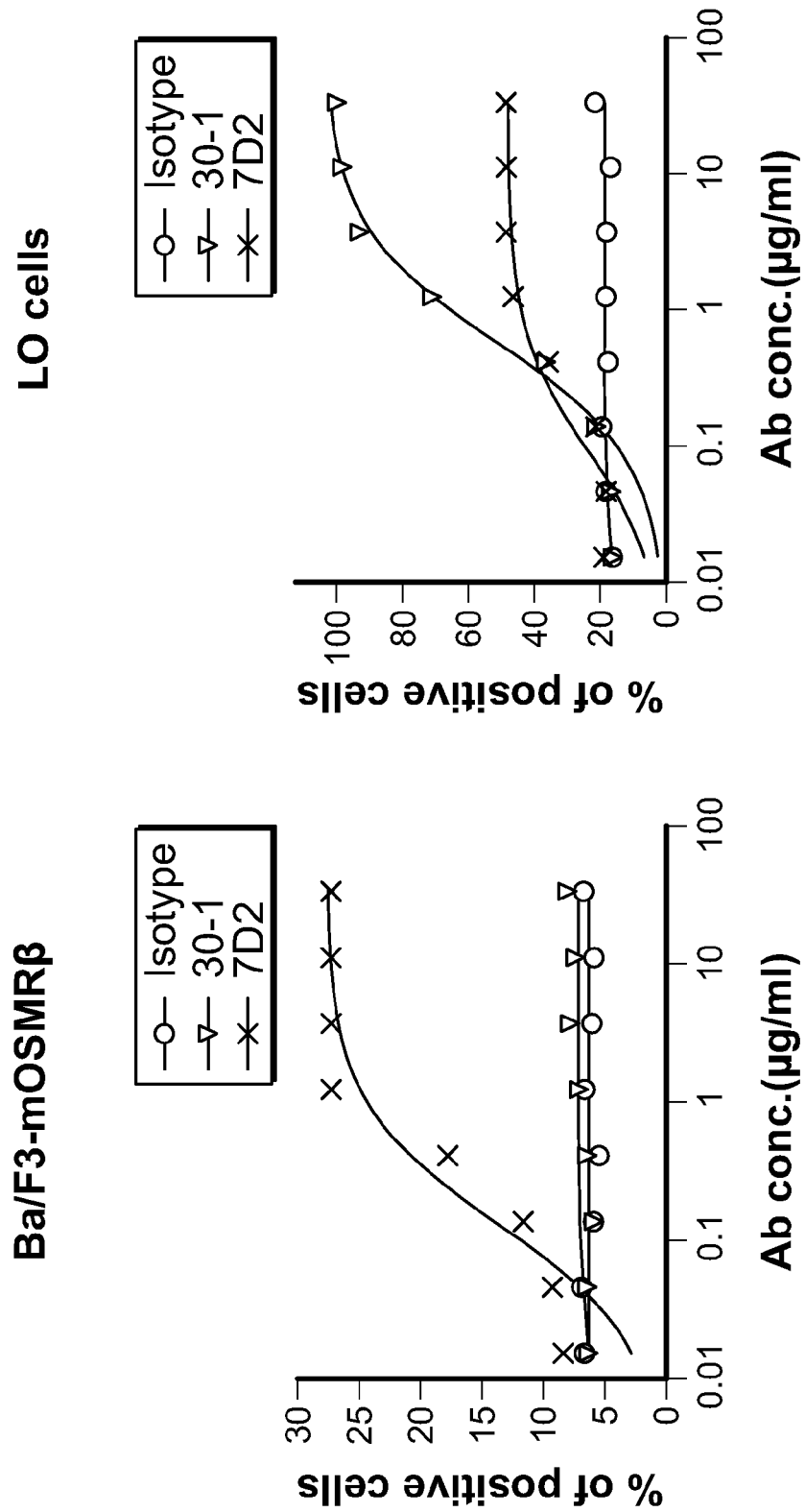

As a consequence, 7D2 monoclonal antibody exhibited better staining to BaF3-mOSMRβ cells compared to commercially available anti-OSMR antibody 30-1, indicating that 7D2 monoclonal antibody had higher affinity to OSMRβ than 30-1. Functional OSM receptor consists of OSMRβ and gp130. LO cells proliferate in response to OSM and express both OSMRβ and gp130 on its cell surface (Hara et al., 1999). LO cells staining suggested that 30-1 had a higher affinity to OSMRβ and gp130 complex than to mOSMRβ monomer (FIGS. 3A and 3B). In contrast, 7D2 monoclonal antibody had a less affinity to OSMRβ/gp130 complex than 30-1. Taken together, 7D2 monoclonal antibody is specifically bound to OSMRβ but not to gp130 or IL-31 Ra.

Example 4

Ex Vivo Characterization of Anti-mOSMRβ Antibody (7D2 Monoclonal Antibody)

Figure 3C:
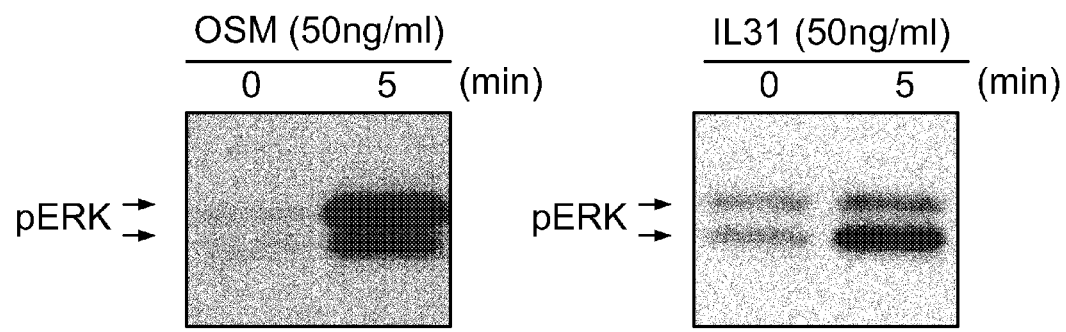
FIGS. 3C and 3D show the results of western blot analysis for Extracellular Signal-regulated Kinases (Erk). Upper and lower arrows indicate phosphorylated Erk1 and Erk2, respectively. Phosphorylated Erk1 and Erk2 were detected by using the specific antibody against phosphorylated Erk1 and Erk2 (i.e., anti-phospho-p44/42 MAP kinase (Thr202/Tyr204) antibody).

LO transfectants exogenously expressing IL-31Ra were constructed in the same manner as Ba/F3 transfectants. Accordingly, the LO transfectants express the OSM receptor (i.e., combination of mOSMRβ and gp130) as well as the IL-31 receptor (i.e., combination of mOSMRβ and IL-31Ra). Five minutes after incubation with 50 ng/ml of OSM or with 50 ng/ml of IL-31, the LO transfectants were confirmed to exhibit phosphorylation of Erks, as shown in FIG. 3C.

Figure 3D:
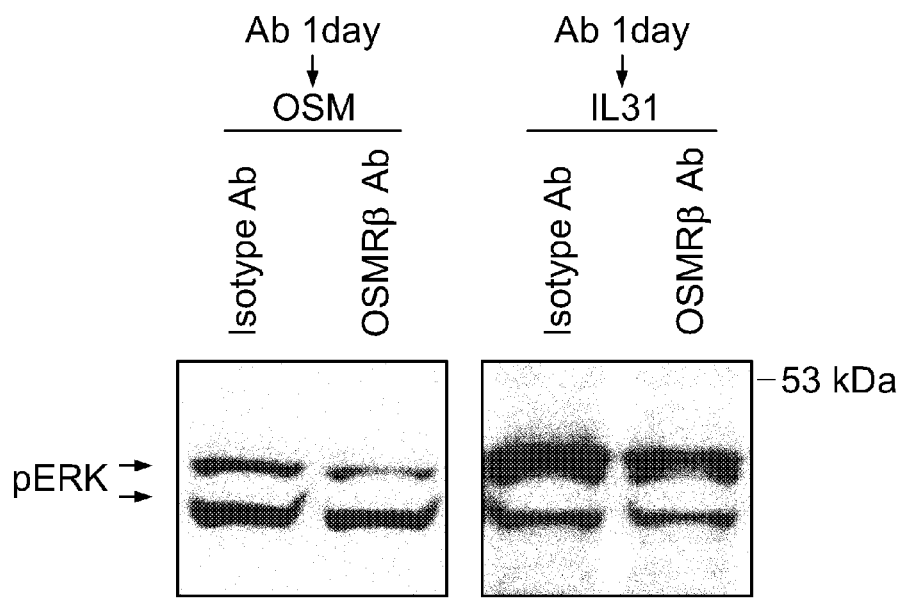

To evaluate the effect of 7D2 monoclonal antibody on the phosphorylation, the phosphorylation of Erks in the LO transfectants was induced by OSM or IL-31 one day after the LO transfectants were per-incubated with 7D2 monoclonal antibody. As a result, approximately 50% of Erk phosphorylation was reduced by pre-incubation (FIG. 3D). On the other hand, pre-incubation of isotype control antibody did not reduce the Erk phosphorylation. These results indicate that 7D2 monoclonal antibody is useful as an inhibitor of both signal pathways of OSM/OSM receptor and IL-31/IL31 receptor.

Example 5

Intradermal Injection of Cytokines in Mice

The mice were housed in individual cages for 3 days. The mice were injected with PBS (40 µl), IL-31 (25-1000 ng/40 µl, Peprotech, Rocky Hill, N.J.), or OSM (400 ng/40 µl, R & D Systems, Minneapolis, Minn.) in the rostral part of the back skin intradermally.

Measurement of Scratching Behavior

The scratching behavior from the hind toes was detected and evaluated using MicroAct (Neuroscience, Tokyo, Japan). The use of MicroAct devices was validated as described elsewhere (Inagaki et al., 2002 & 2003; Takano et al, 2003). Mice were deeply anesthetized with intraperitoneal injection of sodium pentobarbital at a dose of 50 mg/kg body weight. Under sterile conditions, small Teflon-coated magnets (1 mm diameter, 3 mm length) were implanted subcutaneously into the dorsal side of both hind paws of the mice before recording the scratching behavior. After recovery from the anesthesia, the mice with magnets were placed in the observation chamber (11 cm diameter, 18 cm height) for 1 hour to calm the animals. The extent of the recording time was 2 hours. The MicroAct analysis program was used with the following setting to resister the number of long-lasting (>1.5 s) scratch events as described previously (Takano et al., 2003): Threshold (V) 0.1, Event Gap (s) 0.2, Max Freq (Hz) 20.0, Min Freq (Hz) 2.0, Min Duration (s) 1.5.

Example 6

Implantation of Antibody-Incorporated Hydrogel in NC/Nga Mice

A cross-linked gelatin hydrogel (MedGel; MedGel, Kyoto, Japan) that permitted the controlled release of antibodies was cut and soaked in the solution containing isotype control antibody or anti-OSMRβ antibody (7D2 monoclonal antibody) at 4° C. overnight. The implantation was performed twice with an interval of two weeks. For the first implantation, 20 µg (20 µl) of antibodies were soaked in 2 mg of MedGel, and 100 µg (100 µl) of antibodies were soaked in 10 mg of MedGel for the second implantation. Isotype control antibody- and anti-OSMRβ 7D2 monoclonal antibody-soaked MedGel were then implanted into the back of the nape subcutaneously.

Clinical Assessment

The severity of skin lesion were examined and scored, according to the standard as described by Grimstad et al (2008) with some modifications. The severity of the lesion was graded on a scale of 0 to 3 (0=normal skin, 1=scaly and dry, 2=nodular lesions, 3=bloody lesion's) for the six parts of the body (right face, left face, right ear, left ear, scalp, and back). The total score (minimum 0, maximum 18) of each mouse was taken as the score for that mouse. Changes of the score from day 0 of the experimental period were shown in the results.

Measurement of Serum IgE and IL-13 Levels

To measure serum IgE and IL-13 before and at the end-point of the experiment, mice were bled from the tail vein, and the serum was allowed to separate. Serum IgE and IL-13 was measured using an IgE enzyme-linked immunosorbent assay (ELISA) kit (Morinaga, Tokyo, Japan) and an IL-13 ELISA kit (R & D Systems), respectively, according to the manufacturer's instruction.

Histological Analysis

At the end-point of the experiment, the mice were deeply anaesthetized with diethyl ether and transcardially perfused with 0.85% NaCl, followed by ice-cold modified Zamboni's fixative (2% PFA and 0.2% picric acid in 0.1 M PBS, pH 7.4). The skins of the back, face, and ear were quickly removed, postfixed in the same fixative at 4° C. for 3 h, and cryoprotected in 20% sucrose in 0.1 M PBS. All specimens were embedded in O.C.T. medium (Sakura Finetek, Torrance, Calif.), frozen rapidly in cold n-hexane on dry ice, and then were stored at −80° C. Frozen sections were cut on a cryostat (6-µm thickness) and stained with hematoxylin and eosin.

Statistical Analysis

The results are shown as the means±SEM. Statistically significant differences between groups were analyzed by a Student's t-test or analysis of variance (ANOVA) followed by the post-hoc Bonferroni test. The criterion for statistical significance was P<0.05.

Induction of Scratching Behavior by IL-31

IL-31 is suggested to be involved in development of atopic dermatitis by inducing itches. IL-31Ra pairs with OSMRβ to form the functional heterodimer for transducing the IL-31 signaling (Dreuw et al., 2004). Further, it was demonstrated that IL-31Ra and OSMRβ were co-expressed on neurons at dorsal root ganglia (Bando et al., 2006), suggesting that OSM and/or IL-31 may play roles for the induction of itches at the neurons during atopic dermatitis development. To examine the direct effects of IL-31 on scratching behavior in mice, the present inventors injected IL-31 in the rostral part of the back-skin subcutaneously. As shown in FIG. 1A, the number of scratch events by IL-31 began to increase at a dose of 100 ng, reached a peak at a dose of 400 ng, and was maintained at a dose of 1000 ng. In contrast to IL-31, OSM did not induce any increases in the number of scratch events (FIG. 1A). To investigate the effects of OSMRβ deficiency on IL-31-induced scratching behavior, further the present inventors injected IL-31 to OSMRβ$^{-/-}$ mice. Increased number of scratching behavior by IL-31 in OSMRβ$^{+/+}$ mice was completely abolished in OSMRβ$^{-/-}$ mice (FIG. 1B), indicating that IL-31-induced scratching behavior mediates itches through OSMRβ.

Figure 4:
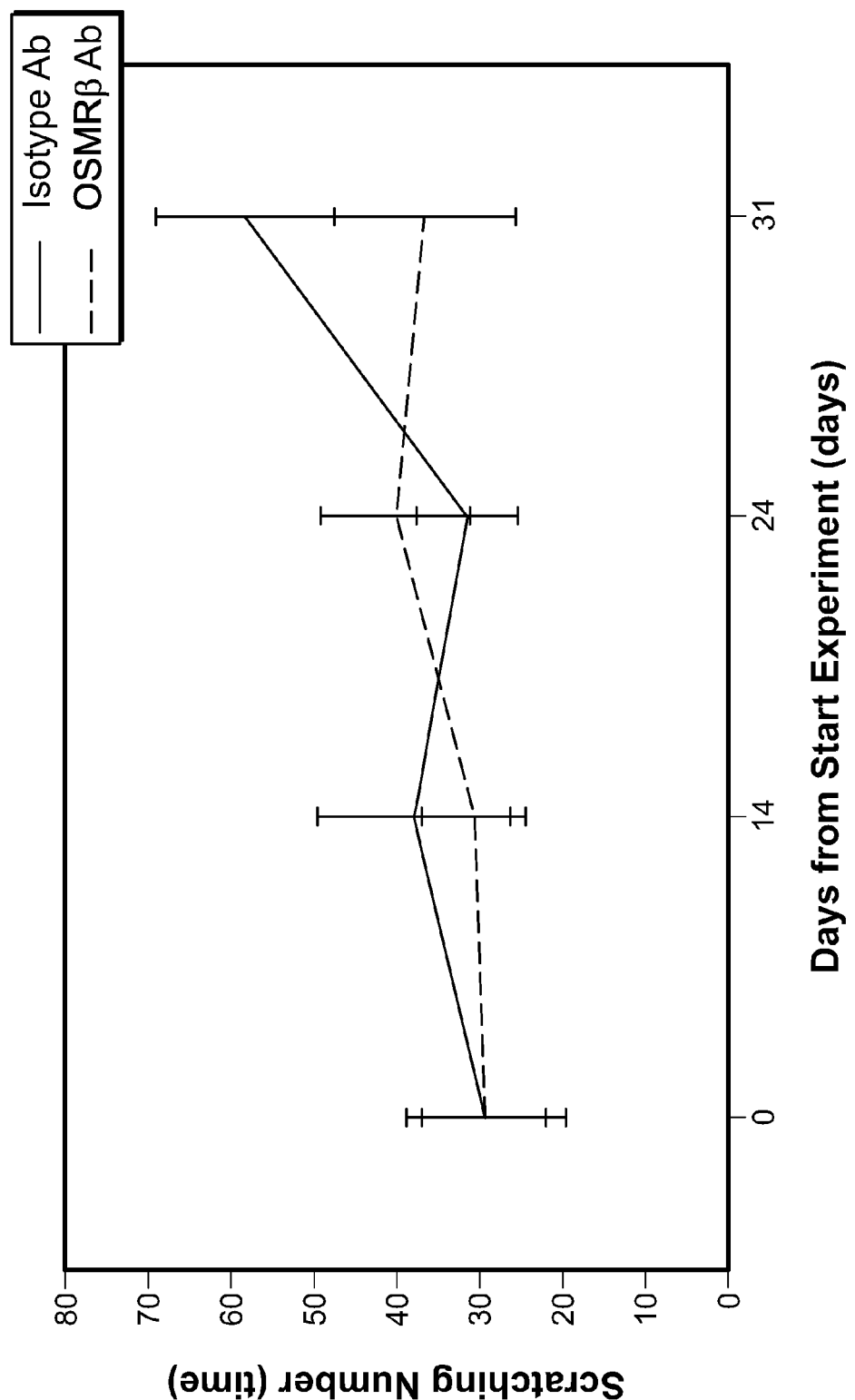
FIG. 4 shows effects of an anti-OSMRβ antibody on scratching behavior of NC/Nga mice. NC/Nga mice were implanted with the hydrogel incorporated with anti-OSMRβ

Effects of an Anti-OSMRβ Antibody (7D2 Monoclonal Antibody) on Scratching Behavior of NC/Nga Mice Based on the data of FIGS. 1A and 1B, the present inventors hypothesize that blockade of the signaling through OSMR by anti-OSMRβ antibody may ameliorate the pruritus of NC/Nga mice. First, the present inventors examined the effects of an anti-OSMRβ antibody (7D2 monoclonal antibody) on the scratching behavior of NC/Nga mice. The MedGel with anti-OSMRβ 7D2 monoclonal antibody or isotype control antibody was implanted subcutaneously into the back of the nape of NC/Nga mice. As shown in FIG. 4, there were no differences in the number of scratching behavior until 24 days of the experimental period between NC/Nga mice implanted with anti-OSMRβ 7D2 monoclonal antibody (OSMRβ-NC/Nga mice) and NC/Nga mice implanted with isotype control antibody (Isotype-NC/Nga mice). However, the number of scratching behavior was tends to increase in Isotype-NC/Nga mice but not in OSMRβ-NC/Nga mice from 24 days to 31 days of the experimental period (FIG. 4). This suggests that anti-OSMRβ 7D2 monoclonal antibody treatment may play role for the blockage of itches during atopic dermatitis development in some aspects.

Effects of Anti-OSMRβ Antibody (7D2 Monoclonal Antibody) on Dermatitis Development of NC/Nga Mice Finally, the present inventors evaluated the effect of anti-mOSMRβ specific antibody (7D2 monoclonal antibody) on dermatitis development in NC/Nga mice. The dermatitis score was clinically assessed and severity of skin damage was histologically evaluated. The skin lesions of Isotype-NC/Nga mice were developed throughout the experimental period (FIG. 5, A-C), while the skin lesions of OSMRβ-NC/Nga mice were improved (FIG. 5, D-F). The skin conditions were evaluated by artificial skin severity score, and the results are shown in FIGS. 6 (A) and (B). The skin severity score in Isotype-NC/Nga mice gradually increased throughout the experimental period. In contrast, the skin severity score in OSMRβ-NC/Nga mice were slightly decreased during 14 days after the first implantation, and drastically decreased after the second implantation (FIG. 6(A)). In addition, the body weight in OSMRβ-NC/Nga mice was increased compared to that in Isotype-NC/Nga mice (FIG. 6(B)).

Histologically, moderate acanthosis and infiltration of inflammatory cells were observed in the back and ear of Isotype-NC/Nga mice. In addition, severe ulcer and infiltration of inflammatory cell were observed in the face of Isotype-NC/Nga mice. On the other hand, these lesions were clearly ameliorated in OSMRβ-NC/Nga mice (FIG. 7). Taken together, these results clearly indicate anti-OSMRβ specific antibody (7D2 monoclonal antibody) can prevent atopic dermatitis development in NC/Nga mice.

Effects of Anti-OSMRβ Antibody (7D2 Monoclonal Antibody) on Serum IgE and IL-13 Concentration in NC/Nga Mice In NC/Nga mice, skin lesions are usually associated with elevated serum IgE levels and Th2-predominant immunoresponses (Inoue et al., 2007) which usually observed in the patient of atopic dermatitis (Cooper et al., 1994). Before the antibody treatment, there were no significant differences in the levels of serum IgE between OSMRβ-NC/Nga mice and Isotype-NC/Nga mice (FIGS. 8 (A) and (B)). After the treatment, contrast to the level of IgE in Isotype-NC/Nga mice, the increase of serum IgE was abolished in OSMRβ-NC/Nga mice (FIG. 8(A)). In addition, the serum IL-13 levels were drastically decreased in OSMRβ-NC/Nga mice after the treatment while this cytokine levels were increased in Isotype-NC/Nga mice (FIG. 8(B)). These results indicate that inflammatory response during atopic dermatitis development was also prevented by the treatment with anti-OSMRβ 7D2 monoclonal antibody.

Comparison of an Anti-OSMRβ Antibody 7D2 and Anti-OSMR Complex Antibody 30-1 on Dermatitis Development of NC/Nga Mice The present inventors evaluated the effect of 7D2 and 30-1 on dermatitis development in NC/Nga mice. The severity of skin damage was histologically evaluated. The skin severity score in 30-1 antibody implanted mice gradually increased throughout the experimental period. In contrast, the skin severity score in 7D2 implanted mice were drastically decreased (FIG. 9). As described above, 7D2 monoclonal antibody is specifically bound to OSMRβ but not to gp130 or IL-31Ra. In contrast, 30-1 monoclonal antibody has higher affinity to OSMRβ/gp130 complex than that to OSMRβ monomer. Actually, 30-1 antibody barely bound to OSMRβ monomer (FIG. 3). These data suggest that the antibodies to OSMRβ/gp130 complex, which are like 30-1, don't block atopic dermatitis development and only OSMRβ specific antibody as 7D2 can prevent skin inflammation under the dermatitis development.

Taken together, the present inventors' findings indicate that anti-OSMRβ specific antibody is a good candidate for the treatment of atopic dermatitis. It has been demonstrated that anti-IL-31 antibody only reduced scratching behavior in same mice model and dermatitis development was not improved by anti-IL-31 antibody treatment. This suggests that blockage of IL-31 alone is not enough to prevent dermatitis development. Both IL-31 and OSM shares OSMRβ as receptor signaling component. Thus, the role of both IL-31 and OSM will be regulated by targeting to OSMRβ with anti-OSMRβ antibody.

In another embodiment, the present inventions provide a method for isolation and identification of an alternative molecule possessing more potent binding or inhibition activities in comparison with 7D2 monoclonal antibody, comprising the following steps:
(1) preparing and incubating a candidate molecule with the cells expressing OSMRβ alone, OSM receptor, IL-31 receptor, and/or combination thereof, in the presence of 7D2 monoclonal antibody,
   wherein said molecule may include small chemical compounds; proteins including antibodies as well as small peptide consisting of approximately 5~20 a.a.; and nucleic acids including aptamers, but should not be restricted thereto;
   wherein the cells expressing OSMRβ alone may be a BaF3 transfectant expressing OSMRβ; the cells expressing OSM receptor may be LO cells; and the cells expressing OSM receptor and IL-31 receptor may be a LO transfectant expressing IL-31Ra; and
(2) indirectly investigating whether said candidate molecule can competitively bind to the cells by measuring the binding of 7D2 monoclonal antibody to the cells In another embodiment, the present inventions provide a method for isolation and identification of an alternative molecule possessing more potent inhibition activity in comparison with 7D2 monoclonal antibody, comprising the following steps:
(1) preparing and incubating a candidate molecule with the cells expressing OSM receptor, IL-31 receptor or both
   wherein said molecule may include small chemical compounds; proteins including antibodies as well as small peptide consisting of approximately 5~20 a.a.; and nucleic acids including aptamers, but should not be restricted thereto;
   wherein the cells expressing OSM receptor may be LO cells; and the cells expressing OSM receptor and IL-31 receptor may be a LO transfectant expressing IL-31Ra; and
(2) investigating whether said candidate molecule can more significantly suppress the phosphorylation activity induced by signal transduction from OSM to OSM receptor and/or from IL-31 to IL-31 receptor in comparison with 7D2 monoclonal antibody.

INDUSTRIAL APPLICABILITY

Consequently, OSMRβ specific 7D2 monoclonal antibody clearly prevented dermatitis development in mice model, suggesting that anti-OSMRβ antibody is a new potential therapeutic approach for the treatment of atopic dermatitis during the onset of clinical skin manifestations.

CROSS REFERENCE

The whole contents of the following cited references are included in the disclosure of this Description.

REFERENCES (1) Bando T, Morikawa Y, Komori T, Senba E (2006) Complete overlap of interleukin-31 receptor A and oncostatin M receptor β in the adult dorsal root ganglia with distinct developmental expression patterns. *Neuroscience* 142: 1263-1271.
(2) Bilsborough J, Leung D Y, Maurer M, Howell M, Boguniewcz M, Yao L, Storey H, Leciel C, Harder B, Gross J A (2006) IL-31 is associated with cutaneous lymphocyte antigen-positive skin homing T cells in patients with atopic dermatitis. *J Allergy Clin Immunol* 117: 418-425.
(3) Cooper K D (1994) Atopic dermatitis: recent trends in pathogenesis and therapy. *J Invest Dermatol* 102: 128-137.
(4) Dillon S R, Sprecher C, Hammond A, Bilsborough J, Rosenfeld-Franklin M, Presnell S R, Haugen H S, Maurer M, Harder B, Johnston J, Bort S, Mudri S, Kuijper J L, Bukowski T, Shea P, Dong D L, Dasovich M, Grant F J, Lockwood L, Levin S D, LeCiel C, Waggie K, Day H, Topouzis S, Kramer J, Kuestner R, Chen Z, Foster D, Parrish-Novak J, Gross J A (2004) Interleukin 31, a cytokine produced by activated T cells, induces dermatitis in mice. *Nat. Immunol* 5: 752-760.
(5) Dreuw A, Radtke S, Pflanz S, Lippok B E, Heinrich P C, Hermanns H M (2004) Characterization of the signaling capacities of the novel gp130-like cytokine receptor. *J Biol Chem* 279: 36112-36120.
(6) Grimstad O, Sawanobori Y, Vestergaad C, Bilsborough J, Olsen U B, Gronhoj-Larsen C, Matsushima K (2008) Anti-interleukin-31-antibodies ameliorate scratching behavior in NC/Nga mice: a model of atopic dermatitis. *Exp Dermatol* 18: 35-43.
(7) Hara T, Nakano Y, Tanaka M, Tamura K, Sekiguchi T, Minehata K, Copeland N G, Jenkins N A, Okabe M, Kogo H, Mukouyama Y, Miyajima A (1999) Identification of podocalyxin-like protein 1 as a novel cell surface marker for hemangioblasts in the murine aorta-gonad-mesonephros region. *Immunity* 11: 567-78.
(8) Inoue J, Aramaki Y (2007) Suppression of skin lesions by transdermal application of CpG-oligodeoxynucleotides in NC/Nga mice, a model of human atopic dermatitis. *J Immunol* 178: 584-591.
(9) Sonkoly E, Muller A, Lauerma A I, Pivarcsi A, Soto H, Kemeny L, Alenius H, Dieu-Nosjean M C, Meller S, Rieker J, Steinhoff M, Hoffmann T K, Ruzicka T, Zlotnik A, Homey B (2006) IL-31: A new link between T cells and pruritus in atopic skin inflammation. *J Allergy Clin Immunol* 117: 411-417.

(10) Tanaka M, Hara T, Copeland N G, Gilbert D J, Jenkins N A, Miyajima A (1999) Reconstitution of the functional mouse oncostatin M (OSM) receptor: molecular cloning of the mouse OSM receptor beta subunit. *Blood* 93: 804-15.

(11) Tanaka M, Hirabayashi Y, Sekiguchi T, Inoue T, Katsuki M, Miyajima A (2003) Targeted disruption of oncostatin M receptor results in altered hemtopoiesis. *Blood* 102: 3154-3162.

(12) Ogorochi, T., Hara, T., Wang, H. M., Maruyama, K. and Miyajima, A., Monoclonal antibodies specific for low-affinity interleukin-3 (IL-3) binding protein AIC2A: evidence that AIC2A is a component of a high-affinity IL-3 receptor. *Blood* 1992. 79: 895-903.

(13) Tanaka, M., Hara, T., Copeland, N. G., Gilbert, D. J., Jenkins, N. A. and Miyajima, A., Reconstitution of the functional mouse oncostatin M (OSM) receptor: molecular cloning of the mouse OSM receptor beta subunit. *Blood* 1999. 93: 804-815.

The invention claimed is:

1. Hybridoma cell line 7D2, deposited with International Patent Organism Depositary as Accession No. FERM ABP-11380.

2. A monoclonal antibody that binds to oncostatin M receptor beta subunit, wherein the monoclonal antibody is produced by the hybridoma cell line 7D2, deposited with International Patent Organism Depositary as Accession No. FERM ABP-11380.

3. An active fragment of an antibody produced by the hybridoma cell line 7D2, deposited with International Patent Organism Depositary as Accession No. FERM ABP-11380, wherein the active fragment binds to oncostatin M receptor beta subunit and is selected from the group consisting of a Fab, a Fab', an F(ab')2, and an scFv.

4. A method for treating atopic dermatitis, comprising administering to a subject in need thereof a therapeutically effective amount of the monoclonal antibody according to claim 2 with a pharmaceutically acceptable carrier, excipient or diluent.

5. A method for treating atopic dermatitis, comprising administering to a subject in need thereof a therapeutically effective amount of the active fragment according to claim 3 with a pharmaceutically acceptable carrier, excipient or diluent.

* * * * *

SEQUENCE LISTING

<160> NUMBER OF SEQ ID NOS: 6

<210> SEQ ID NO 1
<211> LENGTH: 4835
<212> TYPE: DNA
<213> ORGANISM: Mus musculus

<400> SEQUENCE: 1

```
agttgattca tagctggggc gcggggccgc ctccacacgc ctggacagac gtccgcgccc    60
gttcccctgt gaggccgagg accggcaagg ctccggagca ggtcgccagg cgggtaatca   120
gaccaatggc tttctctgtg gtccttcatc cagccttcct cctggcagtg ctgtccctga   180
gggcatcccg aagcgaagtc ttggaggagc ctttaccatt gactcctgag atacataaag   240
tttcttttca attgaaactt caagaagtga atttagaatg gactgtccca gcccttactc   300
atgaagaatt aaacatgata tttcagatag agatcagtag actgaacata tccaacacca   360
tctgggtgga gaattatagc accactgtga agcgtgaaga agctgtgcgt tggaactgga   420
cgtctgatat cccctttggag tgtgtcaaac atttcataag aatcagggct ctggtagatg   480
acaccaagtc ccttccacag agttcctggg gcaactggag ttcctggaaa gaagttaatg   540
caaaggtttc cgttgaacct gataaatcat taatatttcc taaagacaaa gtgttggaag   600
aaggctccaa tgtcaccatc tgtctgatgt atgggcagaa tgtatataat gtatcctgta   660
agttgcaaga tgagccaatc catggagaac aacttgattc ccacgtgtca ttattaaaat   720
tgaacaatgt agtttttcctt agtgacacag ggacaaacat caattgtcaa gccacgaagg   780
gtcctaaaag aatatttggt actgttctct ttgtctcgaa agtgctcgag gaacctaaga   840
atgtttcctg tgaaacccga gactttaaga cttttggactg ttcatgggaa cctggggtag   900
atacgacttt gacttggcgt aaacaaagat tccaaaacta cactttatgt gaatcgttct   960
ctaagagatg tgaggtttct aactacagga actcctatac ctggcaaatc actgaaggct  1020
cacaggaaat gtataacttt actctcacag ctgaaaacca actaaggaaa agaagtgtca  1080
acattaattt taacctgacc catagagttc atccaaaggc tccgcaggac gtcaccctta  1140
aaattatagg tgctacaaaa gccaacatga cttggaaggt tcactcccat ggaaacaact  1200 acacacttt gtgtcaggtt aaactccaat atggagaagt gattcatgag cacaatgttt  1260
ctgtccacat gagcgcaaac tacctcttca gtgatctgga tccagacaca aagtacaagg  1320
cttttgtgcg ctgtgcaagt gccaaccact tctggaaatg gagcgactgg acccaaaaag  1380
agttcagcac acccgagact gctccctcac aggctcttga tgtatggaga caagtgtggt  1440
cggagaatgg aagacgcatt gtgactttat tctggaagcc actattaaaa tcacaggcca  1500
atggcaaaat catatcctat aatatagttg tagaaaatga agccaaacca actgagtcag  1560
aacactactg tgtctgggca ccagccctca gcacaaacct gagccttgac ctgcaacctt  1620
acaagattcg catcacagcc aacaacagca tggggcatc tcctgagtcc ttgatggtcc  1680
```

```
tttctaatga ttctggacac gaagaggtca aggaaaagac aattaaaggt ataaaggatg    1740
cattcaatat ttcttgggag cccgtatctg gagacacgat gggctatgtt gtggactggt    1800
gtgcacattc ccaggaccaa cgctgtgatt tgcagtggaa gaaccttggt cccaatacca    1860
caagcaccac catcacctca gatgatttta aaccaggcgt ccgttacaac ttcagaattt    1920
ttgaaaggtc tgtggaacac aaagctcggt tagtagagaa acaaagagga tacacccagg    1980
aactggctcc tttggtgaat ccaaaagtgg agattcctta ctcgacccct aactccttcg    2040
ttctaagatg gccagattat gacagcgact tccaggctgg ttttataaaa gggtacctcg    2100
tgtatgtgaa atccaaggag atgcagtgca accaaccctg ggaaaggacc ctccttccag    2160
ataattcagt cctctgtaaa tacgacatca atggctcaga gacaaagaca ctcaccgtgg    2220
aaaaccttca gccagagtcc ctctatgagt ttttcgtcac tccgtacacc agcgctggcc    2280
caggacccaa tgaaacgttc acaaaggtca caactccaga tgcacgctcc cacatgctgc    2340
tgcagatcat actacccatg accctctgcg tcttgctcag catcattgtc tgctactgga    2400
aaagtcagtg ggtgaaggag aagtgctacc ctgacattcc caatccgtac aagagcagca    2460
ttctgtcact cataaaatcc aagaagaatc ctcacttaat aatgaatgtc aaagactgca    2520
ttccagatgt ccttgaagtg ataaacaaag cagaaggcag caagacacag tgtgtaggct    2580
ctgggaaact tcacattgaa gatgtaccca ctaagccgcc aatcgtgcca acagaaaagg    2640
attcctcagg gcctgtgccc tgcatcttct ttgagaattt tacttacgat cagtcagctt    2700
ttgactctgg ttcccatggc ctcattccag tccctaaa agacacagca caccaacttg    2760
gactattggc tccacctaac aagttccaga acgtattaaa aaatgactac atgaagcccc    2820
tggtcgaaag tccaactgaa gaaactagct tgatttatgt gtcacagctg gcttcaccca    2880
tgtgcggaga caaggacacg cttgccacag aaccacccgt gccagtgcat ggttcagagt    2940
ataaaaggca aatggtagtt cccgggagcc tcgcatcacc ttctctgaag gaggataaca    3000 gcttgaccctc aacggtcctc ttaggccaag gtgaacagta acaccacgc agcacaaata    3060 aatgcactcc acacactata ggcactttgg gagatgtagc tgttaccatg ccaacaccac    3120
gtgccctggt tggttccagg ggtgggggtt gagggagac tcattatctg cagtgctgat    3180
ttatcaacga tcactacaga ccaacagact taaggaccat ataatatggt gttcaccctg    3240
aaggcgttcc ctagaaatgg cagatccgag agcatgctga ccttgctatt atttggtcca    3300
ggctcaccct tattgcagta gcttgacata gggtgtacac cagtcatttc gcagagccta    3360
cctactcaaa actacacacc gaggctgtgg tcctaggatt ttgatttgca gcagaaaagc    3420
atcttcttgt aaacttaacc tcacacttaa aagtttaagg gtaaaacaag tgggtcagaa    3480
gttttgatta gcaccgcaag agattgctta ctttgattgt gcagatttat cacatttaat    3540
ggaaaggcta caaactaggt tttggccata ccttgaaatg agaacttgtg gtcactgata    3600
aagcagaaag aactctcttc gtgtctacac cttatgtaac taaccagtaa gatgtgcaaa    3660
tggacaggag actcttcatg cgtctcctgc agtcaaacag gattgcaagg agctccagac    3720
ctgctgccca ggcgactgca tcctgtccaa cagactccag tcttcctctt agttttttga    3780
ctacctcaga acaggaaaaa aaggacattt cattgagtga tgcctttttac atataatata    3840 caccacctcc cgcccctgcc cccaccccaa gctgtatcta gatgacctat ttcacgagct    3900
gatctctgct ttttgcacgc ttggttgtct ggttcaagaa aattctgtct cacattccta    3960
ttgtgctaaa atactatagc cccagaactg ggtataattt aaactgtaga agtcagttgt    4020
gaaggaccca aagcatgtct tttgacaaaa atctacttgg tcctatctgt gggtttcaca    4080
```

-continued

```
tcaagattca accaatttca gaaagaagat attctggaaa aaaaaattgt ctgtactaaa    4140
ttcatagatt tttcttgtta ttccgtaaat aaggtattaa caatttccat agcacttaca    4200
cgcaccaggt attaggccac agcatggagg agtactcact gtatacaatg ctatttttag    4260
gttaaggcct aaacttctga agatcttggt aacagcagag ctcctgtaat caactcctgg    4320
aatgtgccat agaggaatga ctatatgtaa cagctgaaca cttacaccgg ttccttcctc    4380
ttaatgcttg tcacattgca gaccaaggtg gagaggttct cctttttgttg ttagctacgt    4440
gtggtagcag tgatgacttt gtgcgcatgt gcagctgtta agtgctatag catgtgctac    4500
agggtgtggc catagaacat agtaacagca accacgaatg ttcaacacaa gctgtccaat    4560
cttctcttta cgtaatacca agcctttgct agaaagcatg gctacaacct aagctaggat    4620
cagccagtat cttgagtagt ttaggtggga aagactttg ctcactattg cagatgctct    4680
gtttacattt tcttgtcaat ggacttctca ctggaaactt gcacccagaa atgttaatga    4740
cattgatttg tgattttgtt tttcatttca attttggtta aaaataatc cataaaacat    4800
ttctgctgtt tcaataaagc ccaaattaaa acatt                               4835
```

<210> SEQ ID NO 2
<211> LENGTH: 971
<212> TYPE: PRT
<213> ORGANISM: Mus musculus

<400> SEQUENCE: 2

```
Met Ala Phe Ser Val Val Leu His Pro Ala Phe Leu Leu Ala Val Leu
1               5                   10                  15

Ser Leu Arg Ala Ser Arg Ser Glu Val Leu Glu Glu Pro Leu Pro Leu
            20                  25                  30

Thr Pro Glu Ile His Lys Val Ser Phe Gln Leu Lys Leu Gln Glu Val
        35                  40                  45

Asn Leu Glu Trp Thr Val Pro Ala Leu Thr His Glu Glu Leu Asn Met
    50                  55                  60

Ile Phe Gln Ile Glu Ile Ser Arg Leu Asn Ile Ser Asn Thr Ile Trp
65                  70                  75                  80

Val Glu Asn Tyr Ser Thr Thr Val Lys Arg Glu Glu Ala Val Arg Trp
                85                  90                  95

Asn Trp Thr Ser Asp Ile Pro Leu Glu Cys Val Lys His Phe Ile Arg
            100                 105                 110

Ile Arg Ala Leu Val Asp Asp Thr Lys Ser Leu Pro Gln Ser Ser Trp
        115                 120                 125

Gly Asn Trp Ser Ser Trp Lys Glu Val Asn Ala Lys Val Ser Val Glu
    130                 135                 140

Pro Asp Lys Ser Leu Ile Phe Pro Lys Asp Lys Val Leu Glu Glu Gly
145                 150                 155                 160

Ser Asn Val Thr Ile Cys Leu Met Tyr Gly Gln Asn Val Tyr Asn Val
                165                 170                 175

Ser Cys Lys Leu Gln Asp Glu Pro Ile His Gly Gln Leu Asp Ser
            180                 185                 190

His Val Ser Leu Leu Lys Leu Asn Asn Val Val Phe Leu Ser Asp Thr
        195                 200                 205

Gly Thr Asn Ile Asn Cys Gln Ala Thr Lys Gly Pro Lys Arg Ile Phe
    210                 215                 220

Gly Thr Val Leu Phe Val Ser Lys Val Leu Glu Glu Pro Lys Asn Val
225                 230                 235                 240
```

-continued

```
Ser Cys Glu Thr Arg Asp Phe Lys Thr Leu Asp Cys Ser Trp Glu Pro
            245                 250                 255

Gly Val Asp Thr Thr Leu Thr Trp Arg Lys Gln Arg Phe Gln Asn Tyr
                260                 265                 270

Thr Leu Cys Glu Ser Phe Ser Lys Arg Cys Glu Val Ser Asn Tyr Arg
            275                 280                 285

Asn Ser Tyr Thr Trp Gln Ile Thr Glu Gly Ser Gln Glu Met Tyr Asn
        290                 295                 300

Phe Thr Leu Thr Ala Glu Asn Gln Leu Arg Lys Arg Ser Val Asn Ile
305                 310                 315                 320

Asn Phe Asn Leu Thr His Arg Val His Pro Lys Ala Pro Gln Asp Val
                325                 330                 335

Thr Leu Lys Ile Ile Gly Ala Thr Lys Ala Asn Met Thr Trp Lys Val
                340                 345                 350

His Ser His Gly Asn Asn Tyr Thr Leu Leu Cys Gln Val Lys Leu Gln
            355                 360                 365

Tyr Gly Glu Val Ile His Glu His Asn Val Ser Val His Met Ser Ala
        370                 375                 380

Asn Tyr Leu Phe Ser Asp Leu Asp Pro Asp Thr Lys Tyr Lys Ala Phe
385                 390                 395                 400

Val Arg Cys Ala Ser Ala Asn His Phe Trp Lys Trp Ser Asp Trp Thr
                405                 410                 415

Gln Lys Glu Phe Ser Thr Pro Glu Thr Ala Pro Ser Gln Ala Leu Asp
            420                 425                 430

Val Trp Arg Gln Val Trp Ser Glu Asn Gly Arg Arg Ile Val Thr Leu
            435                 440                 445

Phe Trp Lys Pro Leu Leu Lys Ser Gln Ala Asn Gly Lys Ile Ile Ser
        450                 455                 460

Tyr Asn Ile Val Val Glu Asn Glu Ala Lys Pro Thr Glu Ser Glu His
465                 470                 475                 480

Tyr Cys Val Trp Ala Pro Ala Leu Ser Thr Asn Leu Ser Leu Asp Leu
                485                 490                 495

Gln Pro Tyr Lys Ile Arg Ile Thr Ala Asn Asn Ser Met Gly Ala Ser
            500                 505                 510

Pro Glu Ser Leu Met Val Leu Ser Asn Asp Ser Gly His Glu Glu Val
            515                 520                 525

Lys Glu Lys Thr Ile Lys Gly Ile Lys Asp Ala Phe Asn Ile Ser Trp
            530                 535                 540

Glu Pro Val Ser Gly Asp Thr Met Gly Tyr Val Val Asp Trp Cys Ala
545                 550                 555                 560

His Ser Gln Asp Gln Arg Cys Asp Leu Gln Trp Lys Asn Leu Gly Pro
                565                 570                 575

Asn Thr Thr Ser Thr Thr Ile Thr Ser Asp Asp Phe Lys Pro Gly Val
            580                 585                 590

Arg Tyr Asn Phe Arg Ile Phe Glu Arg Ser Val Glu His Lys Ala Arg
        595                 600                 605

Leu Val Glu Lys Gln Arg Gly Tyr Thr Gln Glu Leu Ala Pro Leu Val
        610                 615                 620

Asn Pro Lys Val Glu Ile Pro Tyr Ser Thr Pro Asn Ser Phe Val Leu
625                 630                 635                 640

Arg Trp Pro Asp Tyr Asp Ser Asp Phe Gln Ala Gly Phe Ile Lys Gly
                645                 650                 655
```

```
Tyr Leu Val Tyr Val Lys Ser Lys Glu Met Gln Cys Asn Gln Pro Trp
            660                 665                 670

Glu Arg Thr Leu Leu Pro Asp Asn Ser Val Leu Cys Lys Tyr Asp Ile
        675                 680                 685

Asn Gly Ser Glu Thr Lys Thr Leu Thr Val Glu Asn Leu Gln Pro Glu
    690                 695                 700

Ser Leu Tyr Glu Phe Phe Val Thr Pro Tyr Thr Ser Ala Gly Pro Gly
705                 710                 715                 720

Pro Asn Glu Thr Phe Thr Lys Val Thr Thr Pro Asp Ala Arg Ser His
                725                 730                 735

Met Leu Leu Gln Ile Ile Leu Pro Met Thr Leu Cys Val Leu Leu Ser
            740                 745                 750

Ile Ile Val Cys Tyr Trp Lys Ser Gln Trp Val Lys Glu Lys Cys Tyr
        755                 760                 765

Pro Asp Ile Pro Asn Pro Tyr Lys Ser Ser Ile Leu Ser Leu Ile Lys
    770                 775                 780

Ser Lys Lys Asn Pro His Leu Ile Met Asn Val Lys Asp Cys Ile Pro
785                 790                 795                 800

Asp Val Leu Glu Val Ile Asn Lys Ala Glu Gly Ser Lys Thr Gln Cys
                805                 810                 815

Val Gly Ser Gly Lys Leu His Ile Glu Asp Val Pro Thr Lys Pro Pro
            820                 825                 830

Ile Val Pro Thr Glu Lys Asp Ser Ser Gly Pro Val Pro Cys Ile Phe
        835                 840                 845

Phe Glu Asn Phe Thr Tyr Asp Gln Ser Ala Phe Asp Ser Gly Ser His
    850                 855                 860

Gly Leu Ile Pro Gly Pro Leu Lys Asp Thr Ala His Gln Leu Gly Leu
865                 870                 875                 880

Leu Ala Pro Pro Asn Lys Phe Gln Asn Val Leu Lys Asn Asp Tyr Met
                885                 890                 895

Lys Pro Leu Val Glu Ser Pro Thr Glu Thr Ser Leu Ile Tyr Val
            900                 905                 910

Ser Gln Leu Ala Ser Pro Met Cys Gly Asp Lys Asp Thr Leu Ala Thr
        915                 920                 925

Glu Pro Pro Val Pro Val His Gly Ser Glu Tyr Lys Arg Gln Met Val
    930                 935                 940

Val Pro Gly Ser Leu Ala Ser Pro Ser Leu Lys Glu Asp Asn Ser Leu
945                 950                 955                 960

Thr Ser Thr Val Leu Leu Gly Gln Gly Glu Gln
                965                 970
```

<210> SEQ ID NO 3
<211> LENGTH: 3680
<212> TYPE: DNA
<213> ORGANISM: Mus musculus

<400> SEQUENCE: 3

```
ttagtgccgt tctgtgatca gcctggactt cccgaatata aacttgaaac ttgagtggtt    60
ctcttgagtt gtttatggcc tctcagatga cgactctccc tttaaagctg agtggtgtaa   120
gagaagcaga cgatcaccta tttaattgtg ccattacagt aaatgcaact catttctcag   180
cgtcagtgga agccactgtc cggctcttgg aagtcaaagc tgagctcttc tacactcagt   240
gcacaatgct gaattaatcc aagaaatcca gctgtggctg tctcagtttc tagaaagtca   300
ctctctccaa ctgtgactgc tccaactttg cctccgggtg ggctgtatgg tgctgtgaac   360
```

```
catttaaagc ttcttttaa accttcatga ataacagcct ctgggtgtga acgctggaat    420
aatgtggacc ttggcactgt gggcattctc tttcctctgc aaattcagcc tggcagtcct    480
gccgactaag ccagagaaca tttcctgcgt cttttacttc gacagaaatc tgacttgcac    540
ttggagacca gagaaggaaa ccaatgatac cagctacatt gtgactttga cttactccta    600
tggaaaaagc aattatagtg acaatgctac agaggcttca tattcttttc ccgttcctg     660 tgcaatgccc ccagacatct gcagtgttga agtacaagct caaaatggag atggtaaagt    720
taaatctgac atcacatatt ggcatttaat ctccatagca aaaccgaac cacctataat     780 tttaagtgtg aatccaattt gtaatagaat gttccagata caatgaaaac cgcgtgaaaa    840
gactcgtggg tttcctttag tatgcatgct tcggttcaga actgtcaaca gtagccactg    900
gacggaagtc aattttgaaa actgtaaaca ggtctgcaac ctcacaggac ttcaggcttt    960
cacagaatat gtcctggctc tacgattcag gttcaatgac tcaagatatt ggagcaagtg   1020
gagcaaagaa gaaaccagag tgactatgga ggaagttcca catgtcctgg acctgtggag   1080
aattctggaa ccagcagaca tgaacggaga caggaaggtg cgattgttgt ggaagaaggc   1140
aagaggagcc cccgtcttgg agaaaacatt tggctaccac atacagtact ttgcagagaa   1200
cagcactaac ctcacagaga taaacaacat caccacccag cagtatgaac tgcttctgat   1260
gagccaggca cactctgtgt ccgtgacttc tttaattct cttggcaagt cccaagaggc    1320
catcctgagg atcccagatg tccatgagaa gaccttccag tacattaaga gcatgaaggc   1380
ctacatagcc gagcccctgt tggtggtgaa ctggcaaagc tccattcctg cggtggacac   1440
ttggatagtg gagtggctcc cagaagctgc catgtcgaag ttccctgccc tttcctggga   1500
atctgtgtct caggtcacga actggaccat cgagcaagat aaactaaaac ctttcacatg   1560
ctataatata tcagtgtatc cagtgttggg acaccgagtt ggagagccgt attcaatcca   1620
agcttatgcc aaagaaggaa ctccattaaa aggtcctgag accagggtgg agaacatcgg   1680
tctgaggaca gccacgatca catggaagga gattcctaag agtgctagga atggatttat   1740
caacaattac actgtatttt accaagctga aggtggaaaa gaactctcca agactgttaa   1800
ctctcatgcc ctgcagtgtg acctggagtc tctgacacga aggacctctt atactgtttg   1860
ggtcatggcc agcaccagag ctggaggtac aacggggtg agaataaact tcaagacatt    1920
gtcaatcagt gtgttgaaa ttgtccttct aacatctcta gttggaggag ccttcttct     1980 acttagcatc aaaacagtga cttttggcct cagaaagcca aaccggttga ctcccctgtg   2040
ttgtcctgat gttcccaacc ctgctgaaag tagtttagcc acatggctcg agatggtttt    2100
caagaagtca aatatgaagg agactggaaa ctctggggac acagaagacg tggtcctaaa    2160
accatgtccc gtcccgcgg atctcattga caagctggta gtgaactttg agaattttct     2220
ggaagtagtt ttgacagagg aagctggaaa gggtcaggcg agcattttgg gaggagaagc    2280
gaatgagtat gtgaccctcc cgtctaggcc cgacggtccc ccagggaaaa gttttaaaga    2340
gccctccgtt ttaactgagg ttgcttctga agactccac agcacgtgtt ccagaatggc     2400
ggacgaggcg tactcagaat tggccaggca gccttcgtct tcctgtcaga gtccagggct    2460
atcgcctccc cgtgaagacc aagctcagaa tccatatttg aaaaattcag tgacaaccag    2520
ggaatttctt gtgcatgaga atatcccaga gcacagcaaa ggagaagtct gagtgctgct    2580
atggcatgaa gtcctcagaa actgagtgga tctcttccct agaaaagaca ccgagacttc    2640
cagaaaccgc ctttgacccc tcctgttca gttggctgct gcgctgccgg gaaattggtg    2700
```

-continued

```
acacagatgt ggacttaggc caggaagaat ggagtccttt acagggcaaa ggaagttact    2760
ttctcctgtg tgctctcaca gaggcccctt gaaatgatgg cctcaagaga agggccaagc    2820
ttcgggcctt aaaggacgcg cccaggtgga tgtgtcagat cttatcccag gaaccaagct    2880
gtcctggcta ttgctgaagc taccctcagg atccaggaca gctgtcttgt tggcacttga    2940
ctctggcagg aacctgatct ctactcttct tctccctgtc tccggacact ttctctcctt    3000
catgcagaga ccaggactag agcggattcc tcatggtatg ccaggctcct cagtccttgc    3060
tcgggctcag gatcttcaac aatgcctttt ctgggacact ccatcaccca cttatattta    3120
ttttttgcaa cattgtggat tgaacccagg gacttggtta tgcgcggtaa gtgtgctacc    3180
catctcactc accccaagtt tattacgcat tgactgctgc taaatcaaga aactccagaa    3240
acctccagta agacactgcc atgggctgtg ggctaggtag caggtcagcc tgctttgtag    3300
gccatttcct ctgtcttgtg ctatacctgg taggagaagg caccaaacag gtgctcggtg    3360
gcttttgttc agagacacat acttggggcc caggggtgct ttctgagcag acctgatag     3420 ggcctcttcc cagccaccct gagtgaggcc tggtgagagg cagcacttag caaccatatt    3480
tctgccttat gaggacttct gccccttggc tgtagccaag cacagagctt gtgacaagaa    3540
ggtgcctttg gcagaaatgc ccatcacggg atctatttgc ttaggcttgg ggaactgcgt    3600
ggcttgtaca cagtgggcca ccctctggcc cctttgtctt gctctcaagc ctgggaagtg    3660
actttaaaaa aaaaaaaaa                                                  3680
```

<210> SEQ ID NO 4
<211> LENGTH: 716
<212> TYPE: PRT
<213> ORGANISM: Mus musculus

<400> SEQUENCE: 4

```
Met Trp Thr Leu Ala Leu Trp Ala Phe Ser Phe Leu Cys Lys Phe Ser
1               5                   10                  15

Leu Ala Val Leu Pro Thr Lys Pro Glu Asn Ile Ser Cys Val Phe Tyr
            20                  25                  30

Phe Asp Arg Asn Leu Thr Cys Thr Trp Arg Pro Glu Lys Glu Thr Asn
        35                  40                  45

Asp Thr Ser Tyr Ile Val Thr Leu Thr Tyr Ser Tyr Gly Lys Ser Asn
    50                  55                  60

Tyr Ser Asp Asn Ala Thr Glu Ala Ser Tyr Ser Phe Pro Arg Ser Cys
65                  70                  75                  80

Ala Met Pro Pro Asp Ile Cys Ser Val Glu Val Gln Ala Gln Asn Gly
                85                  90                  95

Asp Gly Lys Val Lys Ser Asp Ile Thr Tyr Trp His Leu Ile Ser Ile
            100                 105                 110

Ala Lys Thr Glu Pro Pro Ile Ile Leu Ser Val Asn Pro Ile Cys Asn
        115                 120                 125

Arg Met Phe Gln Ile Gln Trp Lys Pro Arg Glu Lys Thr Arg Gly Phe
    130                 135                 140

Pro Leu Val Cys Met Leu Arg Phe Arg Thr Val Asn Ser Ser His Trp
145                 150                 155                 160

Thr Glu Val Asn Phe Glu Asn Cys Lys Gln Val Cys Asn Leu Thr Gly
                165                 170                 175

Leu Gln Ala Phe Thr Glu Tyr Val Leu Ala Leu Arg Phe Arg Phe Asn
            180                 185                 190

Asp Ser Arg Tyr Trp Ser Lys Trp Ser Lys Glu Glu Thr Arg Val Thr
```

-continued

```
            195                 200                 205
Met Glu Glu Val Pro His Val Leu Asp Leu Trp Arg Ile Leu Glu Pro
210                 215                 220

Ala Asp Met Asn Gly Asp Arg Lys Val Arg Leu Leu Trp Lys Lys Ala
225                 230                 235                 240

Arg Gly Ala Pro Val Leu Glu Lys Thr Phe Gly Tyr His Ile Gln Tyr
                    245                 250                 255

Phe Ala Glu Asn Ser Thr Asn Leu Thr Glu Ile Asn Asn Ile Thr Thr
                260                 265                 270

Gln Gln Tyr Glu Leu Leu Leu Met Ser Gln Ala His Ser Val Ser Val
                275                 280                 285

Thr Ser Phe Asn Ser Leu Gly Lys Ser Gln Glu Ala Ile Leu Arg Ile
290                 295                 300

Pro Asp Val His Glu Lys Thr Phe Gln Tyr Ile Lys Ser Met Lys Ala
305                 310                 315                 320

Tyr Ile Ala Glu Pro Leu Leu Val Val Asn Trp Gln Ser Ser Ile Pro
                    325                 330                 335

Ala Val Asp Thr Trp Ile Val Glu Trp Leu Pro Glu Ala Ala Met Ser
                340                 345                 350

Lys Phe Pro Ala Leu Ser Trp Glu Ser Val Ser Gln Val Thr Asn Trp
                355                 360                 365

Thr Ile Glu Gln Asp Lys Leu Lys Pro Phe Thr Cys Tyr Asn Ile Ser
370                 375                 380

Val Tyr Pro Val Leu Gly His Arg Val Gly Glu Pro Tyr Ser Ile Gln
385                 390                 395                 400

Ala Tyr Ala Lys Glu Gly Thr Pro Leu Lys Gly Pro Glu Thr Arg Val
                    405                 410                 415

Glu Asn Ile Gly Leu Arg Thr Ala Thr Ile Thr Trp Lys Glu Ile Pro
                420                 425                 430

Lys Ser Ala Arg Asn Gly Phe Ile Asn Asn Tyr Thr Val Phe Tyr Gln
                435                 440                 445

Ala Glu Gly Gly Lys Glu Leu Ser Lys Thr Val Asn Ser His Ala Leu
450                 455                 460

Gln Cys Asp Leu Glu Ser Leu Thr Arg Arg Thr Ser Tyr Thr Val Trp
465                 470                 475                 480

Val Met Ala Ser Thr Arg Ala Gly Gly Thr Asn Gly Val Arg Ile Asn
                    485                 490                 495

Phe Lys Thr Leu Ser Ile Ser Val Phe Glu Ile Val Leu Leu Thr Ser
                500                 505                 510

Leu Val Gly Gly Gly Leu Leu Leu Ser Ile Lys Thr Val Thr Phe
                515                 520                 525

Gly Leu Arg Lys Pro Asn Arg Leu Thr Pro Leu Cys Cys Pro Asp Val
530                 535                 540

Pro Asn Pro Ala Glu Ser Ser Leu Ala Thr Trp Leu Gly Asp Gly Phe
545                 550                 555                 560

Lys Lys Ser Asn Met Lys Glu Thr Gly Asn Ser Gly Asp Thr Glu Asp
                    565                 570                 575

Val Val Leu Lys Pro Cys Pro Val Pro Ala Asp Leu Ile Asp Lys Leu
                580                 585                 590

Val Val Asn Phe Glu Asn Phe Leu Glu Val Val Leu Thr Glu Glu Ala
                595                 600                 605

Gly Lys Gly Gln Ala Ser Ile Leu Gly Gly Glu Ala Asn Glu Tyr Val
610                 615                 620
```

```
Thr Ser Pro Ser Arg Pro Asp Gly Pro Pro Gly Lys Ser Phe Lys Glu
625                 630                 635                 640

Pro Ser Val Leu Thr Glu Val Ala Ser Glu Asp Ser His Ser Thr Cys
            645                 650                 655

Ser Arg Met Ala Asp Glu Ala Tyr Ser Glu Leu Ala Arg Gln Pro Ser
            660                 665                 670

Ser Ser Cys Gln Ser Pro Gly Leu Ser Pro Pro Arg Glu Asp Gln Ala
            675                 680                 685

Gln Asn Pro Tyr Leu Lys Asn Ser Val Thr Thr Arg Glu Phe Leu Val
            690                 695                 700

His Glu Asn Ile Pro Glu His Ser Lys Gly Glu Val
705                 710                 715
```

<210> SEQ ID NO 5
<211> LENGTH: 1791
<212> TYPE: DNA
<213> ORGANISM: Artificial Sequence
<220> FEATURE:
<223> OTHER INFORMATION: soluble region of OSMR

<400> SEQUENCE: 5

| | | | | | |
|---|---|---|---|---|---|
| gaagtcttgg | aggagccttt | accattgact | cctgagatac | ataaagtttc | ttttcaattg | 60 |
| aaacttcaag | aagtgaattt | agaatggact | gtcccagccc | ttactcatga | agaattaaac | 120 |
| atgatatttc | agatagagat | cagtagactg | aacatatcca | acaccatctg | ggtggagaat | 180 |
| tatagcacca | ctgtgaagcg | tgaagaagct | gtgcgttgga | actggacgtc | tgatatccct | 240 |
| ttggagtgtg | tcaaacattt | cataagaatc | agggctctgg | tagatgacac | caagtcccct | 300 |
| ccacagagtt | cctggggcaa | ctggagttcc | tggaaagaag | ttaatgcaaa | ggtttccgtt | 360 |
| gaacctgata | atcattaat | atttcctaaa | gacaaagtgt | tggaagaagg | ctccaatgtc | 420 |
| accatctgtc | tgatgtatgg | gcagaatgta | tataatgtat | cctgtaagtt | gcaagatgag | 480 |
| ccaatccatg | agaacaact | tgattcccac | gtgtcattat | taaaattgaa | caatgtagtt | 540 |
| ttccttagtg | acacagggac | aaacatcaat | tgtcaagcca | cgaagggtcc | taaaagaata | 600 |
| tttggtactg | ttctctttgt | ctcgaaagtg | ctcgaggaac | ctaagaatgt | ttcctgtgaa | 660 |
| acccgagact | ttaagacttt | ggactgttca | tgggaacctg | ggtagatac | gactttgact | 720 |
| tggcgtaaac | aaagattcca | aaactacact | ttatgtgaat | cgttctctaa | gagatgtgag | 780 |
| gtttctaact | acaggaactc | ctatacctgg | caaatcactg | aaggctcaca | ggaaatgtat | 840 |
| aactttactc | tcacagctga | aaaccaacta | aggaaaagaa | gtgtcaacat | taatttttaac | 900 |
| ctgacccata | gagttcatcc | aaaggctccg | caggacgtca | cccttaaaat | tataggtgct | 960 |
| acaaaagcca | acatgacttg | gaaggttcac | tcccatggaa | acaactacac | actttttgtgt | 1020 |
| caggttaaac | tccaatatgg | agaagtgatt | catgagcaca | atgtttctgt | ccacatgagc | 1080 |
| gcaaactacc | tcttcagtga | tctggatcca | gacacaaagt | acaaggcttt | tgtgcgctgt | 1140 |
| gcaagtgcca | accacttctg | gaaatggagc | gactggaccc | aaaaagagtt | cagcacaccc | 1200 |
| gagactgctc | cctcacaggc | tcttgatgta | tggagacaag | tgtggtcgga | gaatggaaga | 1260 |
| cgcattgtga | ctttattctg | gaagccacta | ttaaaatcac | aggccaatgg | caaaatcata | 1320 |
| tcctataata | tagttgtaga | aaatgaagcc | aaaccaactg | agtcagaaca | ctactgtgtc | 1380 |
| tgggcaccag | ccctcagcac | aaaccctgagc | cttgacctgc | aaccttacaa | gattcgcatc | 1440 |
| acagccaaca | acagcatggg | ggcatctcct | gagtccttga | tggtccttc | taatgattct | 1500 |

-continued

```
ggacacgaag aggtcaagga aaagacaatt aaaggtataa aggatgcatt caatatttct    1560
tgggagcccg tatctggaga cacgatgggc tatgttgtgg actggtgtgc acattcccag    1620
gaccaacgct gtgatttgca gtggaagaac cttggtccca ataccacaag caccaccatc    1680
acctcagatg attttaaacc aggcgtccgt tacaacttca gaattttttga aaggtctgtg    1740 gaacacaaag ctcggttagt agagaaacaa agaggataca cccaggaact g             1791
```

<210> SEQ ID NO 6
<211> LENGTH: 597
<212> TYPE: PRT
<213> ORGANISM: Artificial
<220> FEATURE:
<223> OTHER INFORMATION: soluble region of OSMR

<400> SEQUENCE: 6

```
Glu Val Leu Glu Glu Pro Leu Pro Leu Thr Pro Glu Ile His Lys Val
1               5                   10                  15

Ser Phe Gln Leu Lys Leu Gln Glu Val Asn Leu Glu Trp Thr Val Pro
            20                  25                  30

Ala Leu Thr His Glu Glu Leu Asn Met Ile Phe Gln Ile Glu Ile Ser
        35                  40                  45

Arg Leu Asn Ile Ser Asn Thr Ile Trp Val Glu Asn Tyr Ser Thr Thr
    50                  55                  60

Val Lys Arg Glu Glu Ala Val Arg Trp Asn Trp Thr Ser Asp Ile Pro
65                  70                  75                  80

Leu Glu Cys Val Lys His Phe Ile Arg Ile Arg Ala Leu Val Asp Asp
                85                  90                  95

Thr Lys Ser Leu Pro Gln Ser Ser Trp Gly Asn Trp Ser Ser Trp Lys
            100                 105                 110

Glu Val Asn Ala Lys Val Ser Val Glu Pro Asp Lys Ser Leu Ile Phe
        115                 120                 125

Pro Lys Asp Lys Val Leu Glu Glu Gly Ser Asn Val Thr Ile Cys Leu
    130                 135                 140

Met Tyr Gly Gln Asn Val Tyr Asn Val Ser Cys Lys Leu Gln Asp Glu
145                 150                 155                 160

Pro Ile His Gly Glu Gln Leu Asp Ser His Val Ser Leu Leu Lys Leu
                165                 170                 175

Asn Asn Val Val Phe Leu Ser Asp Thr Gly Thr Asn Ile Asn Cys Gln
            180                 185                 190

Ala Thr Lys Gly Pro Lys Arg Ile Phe Gly Thr Val Leu Phe Val Ser
        195                 200                 205

Lys Val Leu Glu Glu Pro Lys Asn Val Ser Cys Glu Thr Arg Asp Phe
    210                 215                 220

Lys Thr Leu Asp Cys Ser Trp Glu Pro Gly Val Asp Thr Thr Leu Thr
225                 230                 235                 240

Trp Arg Lys Gln Arg Phe Gln Asn Tyr Thr Leu Cys Glu Ser Phe Ser
                245                 250                 255

Lys Arg Cys Glu Val Ser Asn Tyr Arg Asn Ser Tyr Thr Trp Gln Ile
            260                 265                 270

Thr Glu Gly Ser Gln Glu Met Tyr Asn Phe Thr Leu Thr Ala Glu Asn
        275                 280                 285

Gln Leu Arg Lys Arg Ser Val Asn Ile Asn Phe Asn Leu Thr His Arg
    290                 295                 300

Val His Pro Lys Ala Pro Gln Asp Val Thr Leu Lys Ile Ile Gly Ala
305                 310                 315                 320
```

-continued

```
Thr Lys Ala Asn Met Thr Trp Lys Val His Ser His Gly Asn Asn Tyr
            325                 330                 335
Thr Leu Leu Cys Gln Val Lys Leu Gln Tyr Gly Glu Val Ile His Glu
            340                 345                 350
His Asn Val Ser Val His Met Ser Ala Asn Tyr Leu Phe Ser Asp Leu
            355                 360                 365
Asp Pro Asp Thr Lys Tyr Lys Ala Phe Val Arg Cys Ala Ser Ala Asn
    370                 375                 380
His Phe Trp Lys Trp Ser Asp Trp Thr Gln Lys Glu Phe Ser Thr Pro
385                 390                 395                 400
Glu Thr Ala Pro Ser Gln Ala Leu Asp Val Trp Arg Gln Val Trp Ser
            405                 410                 415
Glu Asn Gly Arg Arg Ile Val Thr Leu Phe Trp Lys Pro Leu Leu Lys
            420                 425                 430
Ser Gln Ala Asn Gly Lys Ile Ile Ser Tyr Asn Ile Val Val Glu Asn
            435                 440                 445
Glu Ala Lys Pro Thr Glu Ser Glu His Tyr Cys Val Trp Ala Pro Ala
    450                 455                 460
Leu Ser Thr Asn Leu Ser Leu Asp Leu Gln Pro Tyr Lys Ile Arg Ile
465                 470                 475                 480
Thr Ala Asn Asn Ser Met Gly Ala Ser Pro Glu Ser Leu Met Val Leu
            485                 490                 495
Ser Asn Asp Ser Gly His Glu Glu Val Lys Glu Lys Thr Ile Lys Gly
            500                 505                 510
Ile Lys Asp Ala Phe Asn Ile Ser Trp Glu Pro Val Ser Gly Asp Thr
    515                 520                 525
Met Gly Tyr Val Val Asp Trp Cys Ala His Ser Gln Asp Gln Arg Cys
    530                 535                 540
Asp Leu Gln Trp Lys Asn Leu Gly Pro Asn Thr Thr Ser Thr Thr Ile
545                 550                 555                 560
Thr Ser Asp Asp Phe Lys Pro Gly Val Arg Tyr Asn Phe Arg Ile Phe
                565                 570                 575
Glu Arg Ser Val Glu His Lys Ala Arg Leu Val Glu Lys Gln Arg Gly
            580                 585                 590
Tyr Thr Gln Glu Leu
            595
```